US011666672B2

(12) United States Patent
Hui et al.

(10) Patent No.: US 11,666,672 B2
(45) Date of Patent: Jun. 6, 2023

(54) ANTI-CD33 ANTIBODY-GUIDED IMAGING AND TREATMENT OF ACUTE MYELOID LEUKEMIA

(71) Applicant: CITY OF HOPE, Duarte, CA (US)

(72) Inventors: Susanta Kumar Hui, Duarte, CA (US); Paul J. Yazaki, Duarte, CA (US); Srideshikan Sargur Madabushi, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 501 days.

(21) Appl. No.: 16/691,071

(22) Filed: Nov. 21, 2019

(65) Prior Publication Data
US 2020/0230265 A1    Jul. 23, 2020

Related U.S. Application Data

(60) Provisional application No. 62/770,692, filed on Nov. 21, 2018.

(51) Int. Cl.
| | | |
|---|---|---|
| *A61K 51/10* | (2006.01) | |
| *C07K 16/28* | (2006.01) | |
| *A61N 5/10* | (2006.01) | |
| *A61B 6/00* | (2006.01) | |

(52) U.S. Cl.
CPC ........ *A61K 51/1045* (2013.01); *A61N 5/1039* (2013.01); *C07K 16/2803* (2013.01); *A61B 6/5235* (2013.01); *A61N 2005/1052* (2013.01)

(58) Field of Classification Search
CPC ............ A61K 51/1045; C07K 16/2803; A61N 2005/1052
USPC ....................................................... 424/1.49
See application file for complete search history.

(56) References Cited

U.S. PATENT DOCUMENTS

| 5,730,982 A | 3/1998 | Scheinberg | |
|---|---|---|---|
| 2018/0221512 A1 * | 8/2018 | Yazaki | .................. A61B 34/20 |

FOREIGN PATENT DOCUMENTS

| WO | 91/09058 | 6/1991 | |
|---|---|---|---|
| WO | WO-2015089344 A1 * | 6/2015 | ......... A61K 47/6809 |

OTHER PUBLICATIONS

Magome et al. Int. J. Radiation Oncol. Biol. Phys. 2016, 96, 679-687. (Year: 2016).*
Jillella et al. Bone Marrow Transplant 1999, 23, 1095-1100 (Year: 1999).*
Appelbaum, F. R., et al., "The use of radiolabeled anti-CD33 antibody to augment marrow irradiation prior to marrow transplantation for acute myelogenous leukemia," Transplant. 54:829-833 (1992).
Arimoto, M. K., et al., "Increased bone marrow uptake of 18F-FDG in leukemia patients: Preliminary findings," SpringerPlus 4:521 (2015).
Caron, P. C., et al., "Biological and immunological features of humanized M195 (Anti-CD33) monoclonal antibodies," Cancer Res. 52:6761-6767 (1992).
Caserta, E., et al., "Copper 64-labeled daratumumab as a PET/CT imaging tracer for multiple myeloma," Blood 131(7):741-745 (2018).
Clift, R. A., et al., "Allogenic marrow transplantation in patients with acute myeloid leukemia in first remission: A randomized trial of two irradiation regimens," Blood 76(9):1867-1871 (1990).
Co, M. S., et al., "Chimeric and humanized antibodies with specificity for the CD33 antigen," J. Immunol. 148:1149-1154 (1992).
Cribe, A.S. W. I., et al., "Extramedullary disease in patients with acute myeloid leukemia assessed by (18)F-FDG PET," Eur. J. Haematol. 90:273-278 (2013).
Dohner, H., et al., "Diagnosis and management of acute myeloid leukemia in adults: recommendations from an international expert panel, on behalf of the European LeukemiaNet," Blood 115:453-474 (2010).
Ehninger, A., et al., "Distribution and levels of cell surface expression of CD33 and CD123 in acute myeloid leukemia," Blood Cancer J. 4:e218 (2014).
Godwin, C. D., et al., "Sinusoidal obstruction syndrome following CD33-targeted therapy in acute myeloid leukemia," Blood 129(16):2330-2331 (2017).
Griffeth, L. K., "Use of PET/CT scanning in cancer patients: technical and practical considerations," BUMC Proceedings 18:321-330 (2005).
Han, E. J., et al., "Early assessment of response to induction therapy in acute myeloid leukemia using $^{18}$F-FLT PET/CT," EJNMMI Res. 7:75 (2017).
Hassan, C., et al., "Genetic and epigenetic heterogeneity and the impact on cancer relapse," Exp. Hematol. 54:26-30 (2017).
Kal, H. B., et al., "Biologically effective dose in total-body irradiation and hematopoietic stem cell transplantation," Strahlentherapie und Onkologie 182:672-679 (2006).
Long, M. N., et al., "Causes and imaging features of false positives and false negatives on $^{18}$F-PET/CT in oncologic imaging," Insights Imaging 2:679-698 (2011).
Magome, T., et al., "Whole-body distribution of leukemia and functional total marrow irradiation based on FLT-PET and dual-energy CT," Mol. Imaging 16:1-6 (2017).
Mallampati, S., et al., "Integrated genetic approaches identify the molecular mechanisms of Sox4 in early B-cell development: intricate roles for RAG1/2 and CK1ε," Blood 123(26):4064-4076 (2014).
Mayer, A. T., et al., "Practical immune-PET radiotracer design considerations for human immune checkpoint imaging," J. Nucl. Med. 58:538-546 (2017).

(Continued)

*Primary Examiner* — Michael G. Hartley
*Assistant Examiner* — Sean R Donohue
(74) *Attorney, Agent, or Firm* — Perkins Coie LLP; Lara J. Dueppen; Mengke X. McCullough

(57) ABSTRACT

Disclosed is a non-invasive PET-CT imaging method for detecting acute myeloid leukemia (AML) or extramedullary disease (EMD) in a subject using a radioactive isotope-labeled anti-CD33 antibody. Also disclosed is a PET-CT imaged-guided method for treating AML or EMD.

20 Claims, 18 Drawing Sheets
(16 of 18 Drawing Sheet(s) Filed in Color)
Specification includes a Sequence Listing.

(56) References Cited

OTHER PUBLICATIONS

Pollard, J. A., et al., "Correlation of CD33 expression level with disease characteristics and response to gemtuzumab ozogamicin containing chemotherapy in childhood AML," Blood 119(16):3705-3711 (2012).

Riad, R., et al., "False-positive F-18 FDG uptake in PET/CT studies in pediatric patients with abdominal Burkitt's lymphoma," Nucl. Med. Comm. 31:232-238 (2010).

Shah, A., et al., "Survival and cure of acute myeloid leukaemia in England, 1971-2006: a population-based study," Br. J. Haematol. 162:509-516 (2013).

Stein, A., et al., "Phase I trial of total marrow and lymphoid irradiation transplant conditioning in patients with relapsed/refractory acute leukemia," Biol. Blood Marrow Transplant. 23(4):618-624 (2017).

Stolzel, F., et al., "$^{18}$F-FDG-PET/CT for detection of extramedullary acute myeloid leukemia," Haematologica 96(10):1552-1556 (2011).

Van Der Jagt, R. H.C., et al., "Localization of radiolabeled antimyeloid antibodies in a human acute leukemia xenograft tumor model," Cancer Res. 52:89-94 (1992).

Van Hoof, S. J., et al., "Development and validation of a treatment planning system for small animal radiotherapy: SmART-Plan," Radiother. Oncol. 109:361-366 (2013).

Williams, K. M., et al., "Novel PET imaging with fluorothymidine (FLT) predicts relapse quantitatively at day 28 post transplantation in patients with acute leukemia," Abstracts / Biol. Blood Marrow Transplant. 22:S213-S214 (2016).

\* cited by examiner

Fig. 1E
Fig. 1F
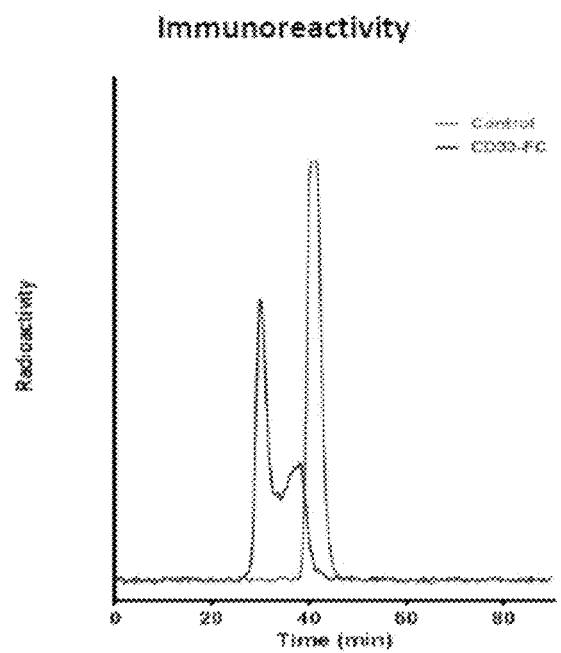
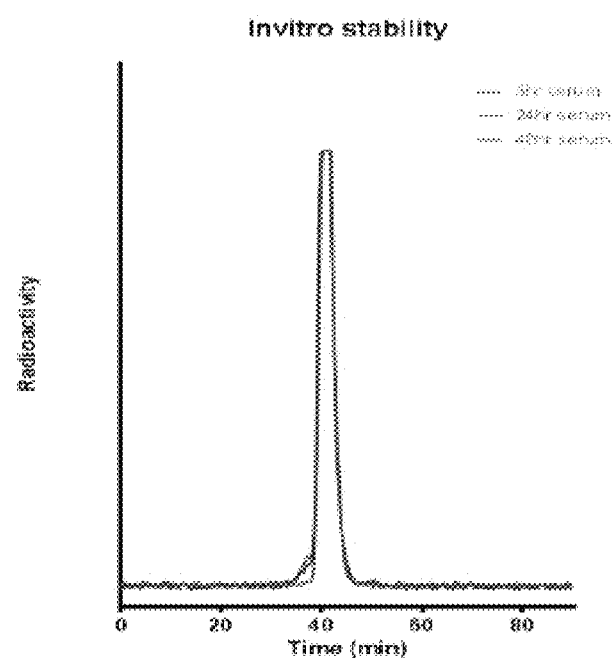
Fig. 1G
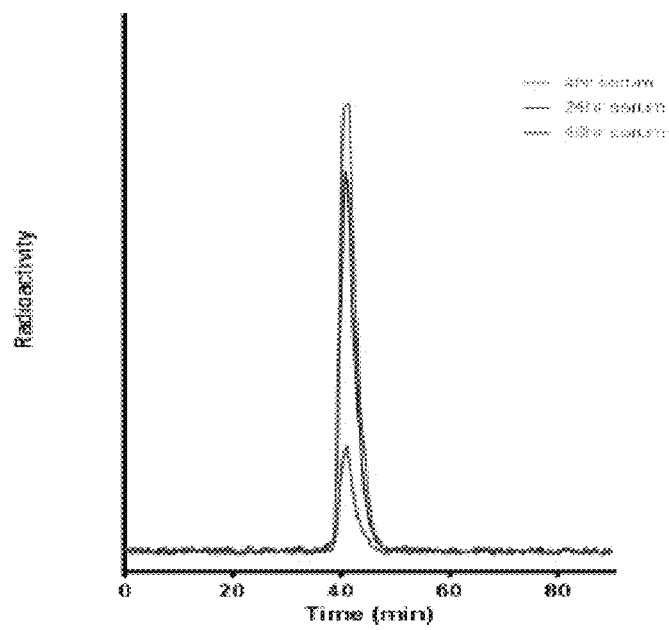

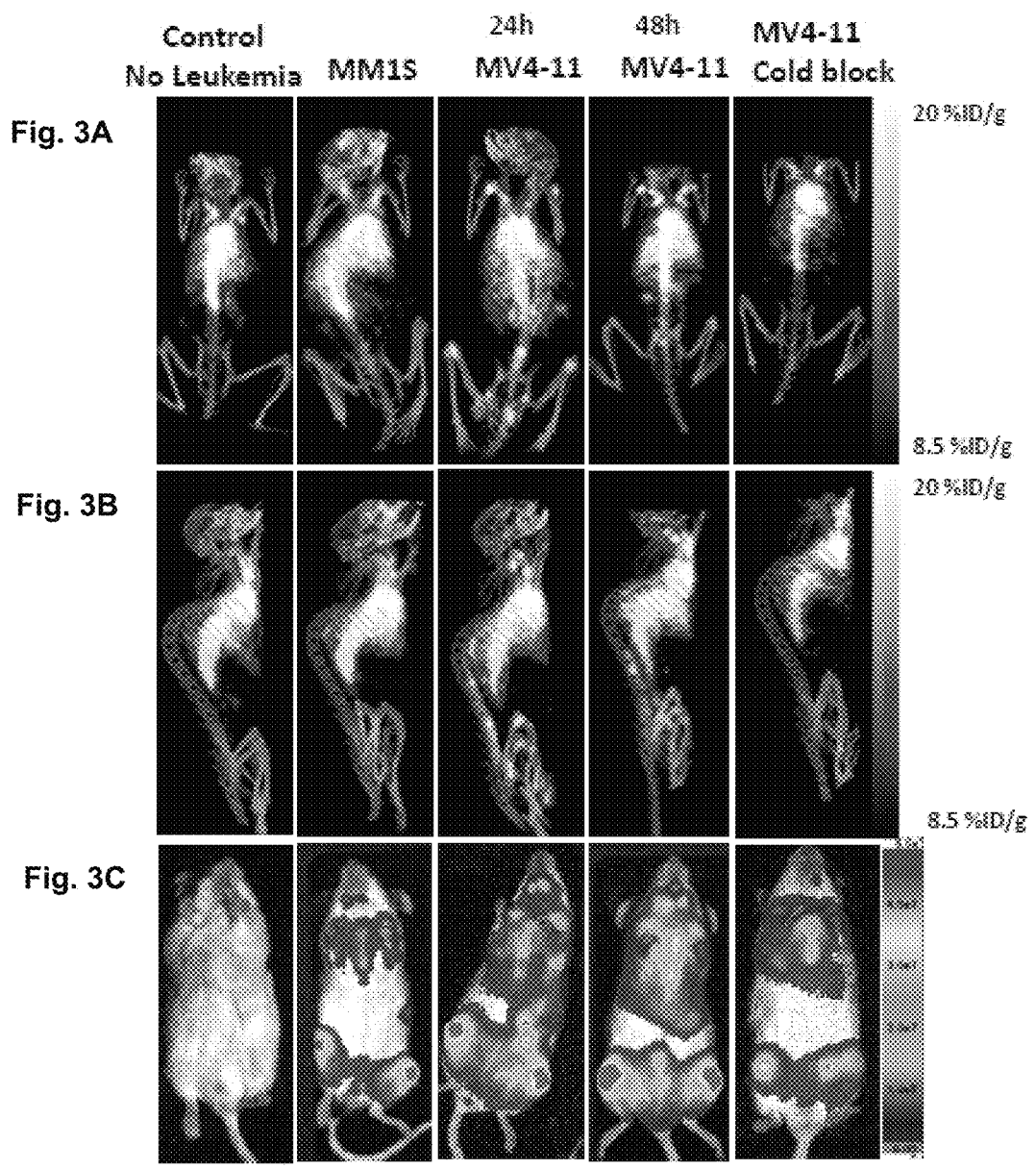

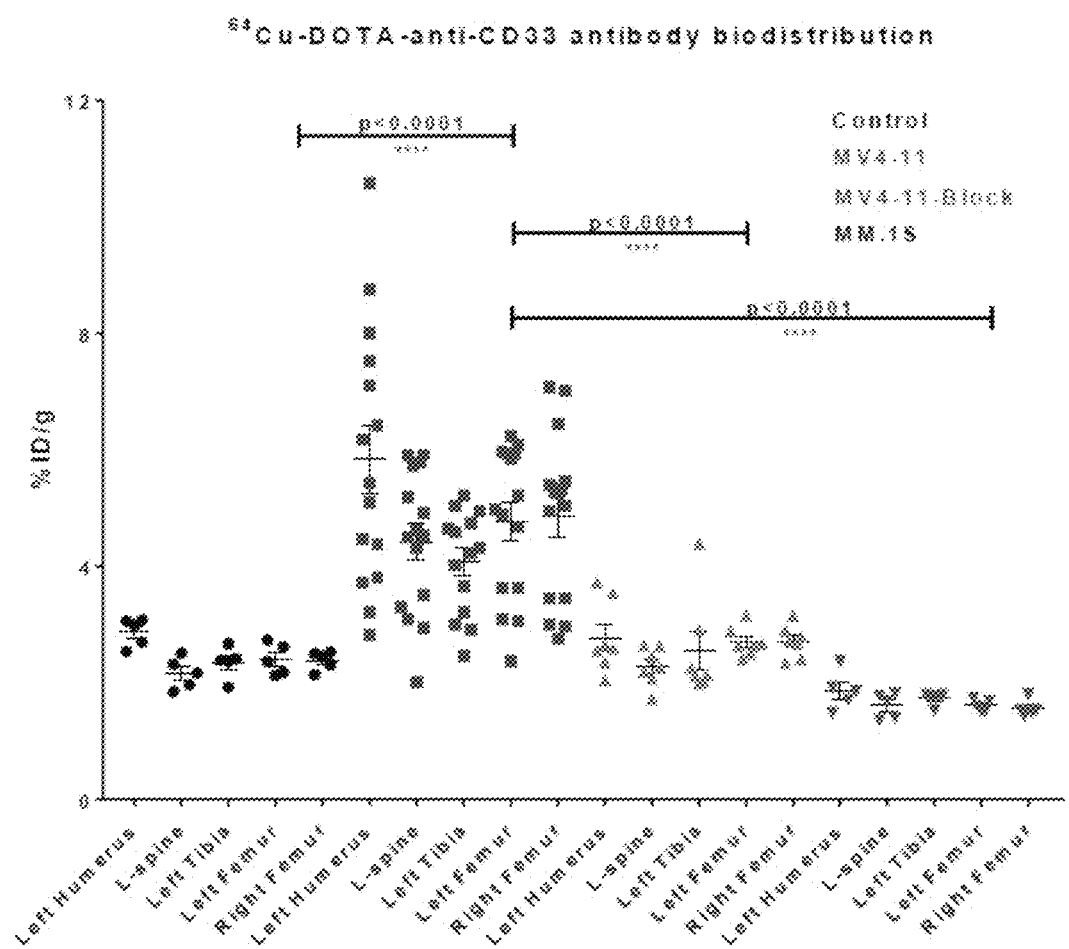

ANTI-CD33 ANTIBODY-GUIDED IMAGING AND TREATMENT OF ACUTE MYELOID LEUKEMIA

PRIORITY CLAIM

This application claims priority to U.S. Provisional Patent Application No. 62/770,692, filed Nov. 21, 2018, which is incorporated herein by reference in its entirety, including drawings.

GOVERNMENT INTEREST

This invention was made with government support under Grant Numbers CA033572 and CA154491, awarded by the National Institutes of Health. The government has certain rights in the invention.

SEQUENCE LISTING

This disclosure includes a sequence listing, which is submitted in ASCII format via EFS-Web, and is hereby incorporated by reference in its entirety. The ASCII copy, created on Jan. 16, 2020, is named SequenceListing.txt and is 3.66 kilobytes in size.

CROSS REFERENCE TO RELATED APPLICATION

This application claims priority to U.S. Provisional Application No. 62/770,692, filed Nov. 21, 2018, which is incorporated herein by reference in its entirety.

FIELD OF THE INVENTION

The present invention relates to the fields of immunology, antibodies and conjugates, molecular biology, PET-CT imaging, cancer diagnosis, and cancer therapy. In particular, this invention provides antibodies for theranostic imaging and treatment of acute myeloid leukemia (AML).

BACKGROUND

AML is a highly aggressive hematopoietic malignancy with an extremely poor prognosis as reflected by an overall 5-year survival rate of 40%-45% in young adults and <10% in the elderly (>65 years of age) [1]. Research over the past decades has helped us understand the pathobiology, classification and genomic landscape of the disease, which has resulted in improving current treatment options. Despite advances, the prognosis for elderly patients who account for the majority of new AML cases remains discouraging [2]. More than 70% of elderly AML patients (>65 years old) will die of their disease within 1 year of diagnosis and treatment [3]. Therefore, new diagnostic and therapeutic approaches are necessary to improve outcomes.

Currently, the diagnostic criteria for AML is the presence of ≥20% blasts in the bone marrow or peripheral blood [4]. AML diagnosis and prognosis are currently achieved by single-point bone marrow biopsies (iliac crest) followed by cytogenetics and mutation analysis. However, the iliac crest biopsy cannot account for heterogeneous bone marrow disease and extramedullary involvement. F18-FDG (metabolic activity) and F18-FLT (cell proliferation) have been tested for diagnosis and monitoring treatment response. However, these PET tracers are non-specific in that they detect metabolic activity or proliferation, which may be affected post treatment and hence yielding non-reliable results. Hence, there is need for new diagnostic tools that are non-invasive, specific and sensitive to AML in the whole body, including extramedullary organs, and useful to longitudinally monitor disease and treatment response.

SUMMARY

In one aspect, discloses herein is a non-invasive method of in vivo detecting acute myeloid leukemia (AML) in a subject. The method entails administering to the subject an effective dose of a radioactive isotope-labeled anti-CD33 antibody, exposing the subject to PET-CT scanning, and detecting CD33− PET-CT signal in tissue or organ of the subject, thereby to determine the presence of the AML cancer cells. In certain embodiments, the PET-CT scanning is carried out about 6 hours, about 12 hours, about 18 hours, about 24 hours, about 30 hours, about 36 hours, or about 48 hours after administration of the radioactive isotope-labeled anti-CD33 antibody. In certain embodiments, the radioactive isotope-labeled anti-CD33 antibody is administered to the subject by intravenous injection, subcutaneous injection, or peritoneal injection. In certain embodiments, the radioactive isotope is conjugated to the anti-CD33 antibody via a chelating agent. In certain embodiments, the chelating agent is 1,4,7,10-tetraazacyclododecane-1,4,7,10-tetraacetic acid (DOTA). In certain embodiments, the radioactive isotope is $^{64}$Cu.

In another aspect, disclosed is a non-invasive method of in vivo detecting extramedullary disease (EMD) in a subject. The method entails administering to the subject an effective dose of a radioactive isotope-labeled anti-CD33 antibody, exposing the subject to PET-CT scanning, and detecting CD33− PET-CT signal in tissue or organ of the subject, thereby to determine the presence of the EMD cancer cells. In certain embodiments, the PET-CT scanning is carried out about 6 hours, about 12 hours, about 18 hours, about 24 hours, about 30 hours, about 36 hours, or about 48 hours after administration of the radioactive isotope-labeled anti-CD33 antibody. In certain embodiments, the radioactive isotope-labeled anti-CD33 antibody is administered to the subject by intravenous injection, subcutaneous injection, or peritoneal injection. In certain embodiments, the radioactive isotope is conjugated to the anti-CD33 antibody via a chelating agent. In certain embodiments, the chelating agent is 1,4,7,10-tetraazacyclododecane-1,4,7,10-tetraacetic acid (DOTA). In certain embodiments, the radioactive isotope is 64Cu.

In yet another aspect, disclosed is a method of determining heterogenicity in the spatial distribution of AML in a subject. The method entails administering to the subject an effective dose of a radioactive isotope-labeled anti-CD33 antibody, exposing the subject to PET-CT scanning; and detecting CD33− PET-CT signal in tissue or organ of the subject, thereby to determine the heterogenicity in the spatial distribution of AML. In certain embodiments, the PET-CT scanning is carried out about 6 hours, about 12 hours, about 18 hours, about 24 hours, about 30 hours, about 36 hours, or about 48 hours after administration of the radioactive isotope-labeled anti-CD33 antibody. In certain embodiments, the radioactive isotope-labeled anti-CD33 antibody is administered to the subject by intravenous injection, subcutaneous injection, or peritoneal injection. In certain embodiments, the radioactive isotope is conjugated to the anti-CD33 antibody via a chelating agent. In certain embodiments, the chelating agent is 1,4,7,10-tetraazacyclododecane-1,4,7,10-tetraacetic acid (DOTA). In certain embodiments, the radioactive isotope is 64Cu.

In yet another aspect, disclosed is a method of treating AML or EMD in a subject. The method entails administering to a subject an effective dose of a radioactive isotope-labeled anti-CD33 antibody, exposing the subject to PET-CT scanning, detecting CD33+ PET-CT signal in tissue or organ of the subject to determine the presence of the cancer cells, and administering fTMI therapy to the subject based on the distribution of the CD33+ PET-CT signal, wherein the tissue or organ with a higher intensity of the CD33+ PET-CT signal receives a higher dose, a higher frequency, or a longer exposure of the fTMI therapy than the tissue or organ with a lower intensity of the CD33+ PET-CT signal. In certain embodiments, the vital organs, or the tissue or organ having no CD33+ PET-CT signal does not receive any fTMI therapy. In certain embodiments, the method further includes administering to the subject a chemotherapy before or after the fTMI therapy. In certain embodiments, the combination of the fTMI therapy and the chemotherapy results in a reduced dose, frequency, and/or intensity of the fTMI therapy or the chemotherapy comparing to each of the therapies used alone. In certain embodiments, the chemotherapy is AraC. In certain embodiments, the PET-CT scanning is carried out about 6 hours, about 12 hours, about 18 hours, about 24 hours, about 30 hours, about 36 hours, or about 48 hours after administration of the radioactive isotope-labeled anti-CD33 antibody. In certain embodiments, the method further includes transplanting bone marrow to the subject. In certain embodiments, the radioactive isotope-labeled anti-CD33 antibody is administered to the subject by intravenous injection, subcutaneous injection, or peritoneal injection. In certain embodiments, the radioactive isotope is conjugated to the anti-CD33 antibody via a chelating agent. In certain embodiments, the chelating agent is 1,4,7,10-tetraazacyclododecane-1,4,7,10-tetraacetic acid (DOTA). In certain embodiments, the radioactive isotope is 64Cu.

BRIEF DESCRIPTION OF THE DRAWINGS

This application contains at least one drawing executed in color. Copies of this application with color drawing(s) will be provided by the Office upon request and payment of the necessary fees.

FIGS. 1A-1G show anti-CD33 mAb antibody conjugated with DOTA, radiolabeling, immunoreactivity and stability. FIG. 1A shows that the murine anti-human CD33 mAb (lane 3), DOTA-anti-human CD33 mAb (lane 5) and DOTA-anti-human CD33 mAb vialed product (lane 7) were analyzed on an iso-electrofocusing gel (Lane 1 and 9, Invitrogen IEF standards). Coomasie Blue staining showed a shift to a more acidic pH, confirming the conjugation process. The unconjugated anti-CD33 antibody showed a family of bands with an isoelectric point (pI) of >6.9. Post-DOTA conjugation, the pI of anti-CD33-DOTA shifted to a more acidic range of ~5.3-5.6. FIG. 1B shows that the DOTA-anti-human CD33 mAb was electrophoresed on a SDS-PAGE gel under non-reducing (lane 3) and reducing conditions (lane 6) demonstrating purity (Lane 1 and 8, see blue plus 2 standard). FIG. 1C shows analysis of $^{64}$Cu-DOTA-anti-CD33 by HPLC size exclusion chromatography (SEC). Radiochromatogram (green) of the purified $^{64}$Cu-DOTA-anti-CD33 shows efficient labeling of anti-CD33-DOTA with Cu-64, with no aggregates and a retention time around 40 minutes corresponding to an intact mAb. FIG. 1D shows $^{64}$Cu-DOTA-anti-CD33 immunoreactivity. The purified $^{64}$Cu-DOTA-anti-CD33 was incubated with soluble CD33-Fc antigen and analyzed by SEC. The radioactivity peak (blue) showed a faster retention time (~30 minutes) indicating a shift to a higher molecular size consistent with binding to CD33 Fc antibody (67-85 kDa). FIG. 1E shows an overlay of SEC radiochromatogram depicting a clear shift in $^{64}$Cu-DOTA-anti-CD33 incubated with CD33-Fc implying CD33 specific immunoreactivity. FIGS. 1F and 1G show that $^{64}$Cu-DOTA-anti-CD33 stability was tested in vitro (FIG. 1F) and in vivo (FIG. 1G) in mouse serum at different time points. SEC chromatogram clearly indicates that the radiolabeled antibody was very stable even at 48 hours.

FIG. 2A shows CD33 cell surface expression in AML and MM cell line using anti-CD33-DOTA dylight-488. MV4-11 and HL-60 cells were 100% positive for CD33 whereas Kg1a had <30% cells positive for CD33. Therefore, for further studies only MV4-11 and HL-60 AML cells were used. FIG. 2B shows CD33 immunofluorescence using anti-CD33-DOTA-dylight 488. AML and MM cells were stained with anti-CD33-DOTA-dylight 488. HL60 and MV4-11 showed CD33 immunofluorescence whereas negative control MM.1S had no CD33 staining. Unstained cells were used to set background, and all images were obtained with the same settings in Zeiss AxioObserver Z1 florescent microscope. FIG. 2C shows histogram representing PE associated florescence (log values) and the interval gates were adjusted around each four bead peaks and labeled as Low, Med Low, Med High and High. FIG. 2D shows linear regression plots for the number of PE molecules per bead (x axis) against fluorescence (y axis) (log 10 values). FIG. 2E shows CD33 antibody per cell in AML and MM cell line. AML HL60 had more CD33 on cell surface than MV4-11 while MM.1S had no CD33 molecules.

FIGS. 3A-3F show PET-CT images and biodistribution of 64Cu-DOTA-anti-CD33 antibody in AML and MM bearing mice. Representative PET-CT and bioluminescence images (BLI) are shown from AML, MM bearing, and no leukemia control mice. Cu-64-anti-CD33-DOTA (10 µg/100 µCi) was injected into these mice via tail vein 24-48 hours before PET-CT imaging or biodistribution was carried out. FIG. 3A shows PET-CT images (coronal) demonstrating CD33 activity in AML bearing mice. FIG. 3B shows PET-CT images (sagittal) demonstrating CD33 activity in AML mice. FIG. 3C shows bioluminescence (BLI) images of AML, cold blocked AML, MM.1S and no leukemia control mice. FIG. 3D shows PET-CT images (coronal) of AML bearing mice highlighting CD33+ regions in the skeletal system. FIGS. 3E and 3F show that biodistribution of 64Cu-DOTA-anti-CD33 in bones and different tissues was conducted 24 hours (FIG. 3E) and 48 hours (FIG. 3F) post injection. Plot of % ID/g of different tissues has been shown, indicating that CD33 activity was high in bones of MV4-11 mice whereas no activity was seen in CD33-MM.1S, cold blocked MV4-11, or no leukemia control mice. The % ID/g between groups was insignificant for blood, heart, liver, lung and kidney. Statistical significance was determined using "t" test and considered significant when <0.05. Biodistribution and imaged PET activity of 64Cu-DOTA-anti-CD33 was presented as the percentage of the injected activity per gram of organ/tissue.

FIG. 6A is the ROC curve showing sensitivity vs 100-specificity for the 64Cu-DOTA-anti-CD33 imaging was generated using biodistribution data (n≥115 mice). The imaging method has a sensitivity of ~95.5% and specificity of 100%. Therefore, this is a very reliable imaging method to detect AML. FIGS. 6B and 6C show correlation curve for % engraftment vs % ID/g for femur (FIG. 6B) and L-spine (FIG. 6C) (n≥5 mice). A very high correlation was observed between leukemia engraftment and Cu-64-anti-CD33 activity in left femur ($R^2$=0.9854) and L-spine ($R^2$=0.8027). Engraftment was determined using flow cytometry. FIG. 6D shows a correlation curve for CD33 PET contour signal vs BLI signal (n≥5 mice). Strong correlation ($R^2$=0.9262) was seen between BLI signal vs PET signal; however, the spatial resolution was high in PET whereas in BLI it was poor. The data was assumed for Gaussian distribution, and Pearson's correlation coefficients were calculated using Prism software. The p value was calculated using two tailed "t" test and considered significant if <0.05.

FIG. 7A shows spatial distribution of AML in femur and tibia. The PET-CT images (coronal) of representative AML bearing mice show preferential niche to the joints in the early stages of the disease. FIG. 7B shows a representative PET CT image (sagittal) of spine from AML bearing mice showing leukemia burden-dependent CD33+ activity. The leukemia was localized in the early disease stage (>10% engraftment); however, with increased leukemic burden (>10%), it spread and appeared systemic.

FIG. 8D shows dose-volume histograms (DVH) of the fTMI treatment plan results for 5 mice receiving 2 Gy TMI with 2 Gy boost. FIG. 8E shows Kaplan Meier curve representing survival of fTMI and/or AraC treated and untreated mice. The data clearly indicate fTMI+AraC treatment increased survival of mice by about 17 days and about 10 days longer than untreated and AraC treated mice, respectively.

FIG. 9A shows Kaplan Meier survival curve for fTMI with chemotherapy treated NSG mice. FIG. 9B shows disease monitoring pre- and post-treatment using BLI. Representative BLI images from different groups pre- and post-treatment. AML mice receiving fTMI treatment with chemotherapy showed decrease in leukemic burden 2 weeks post intervention and subsequently increased median survival (44 days) compared to that of untreated control (28.5 days) or AraC treated mice (32.5 days). The fTMI-chemo study was repeated twice with at least n≥3 mice per group. FIG. 9C shows Kaplan Meier survival curve for fTMI with chemotherapy treated B6 mice. The B6 mice were injected with murine AML cell line MLL-AF9. The B6 mice were more radiation tolerant than NSG and hence received higher doses viz 6 Gy TMI and 3 Gy boost in two fractions (total 12 Gy TMI and 6 Gy boost). Day 3 post radiation, mice were transplanted with 2×10$^6$ total bone marrow cells. fTMI with chemotherapy treated mice had a median survival of ~59 days whereas conventional chemotherapy (AraC) treated mice survived 33 days, and untreated mice survived only 26.5 days.

DETAILED DESCRIPTION

Figure 1A:
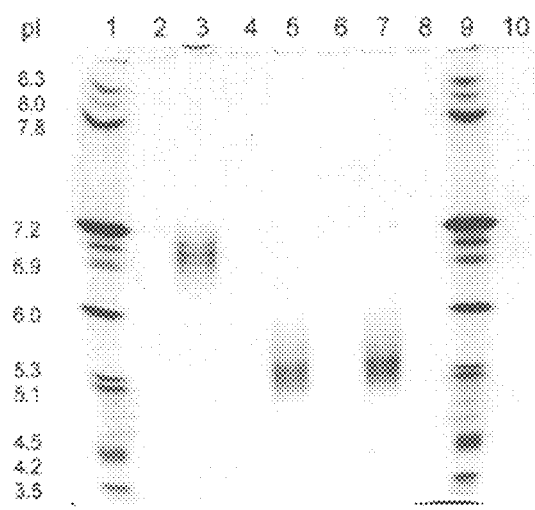

Disclosed herein is an anti-CD33 monoclonal antibody (mAb) used for immuno-positron emission tomography (PET) imaging of AML. CD33 or SIGLEC3 is a cell surface marker found on myeloid stem cells, monoblasts, myeloblasts, monocytes/macrophages, and granulocytic precursors. However, CD33 is not expressed on erythrocytes, platelets, B-cells, T-cells, or NK cells, making it a suitable myeloid marker and therefore commonly used in the diagnosis of AML. CD33 has been shown to be expressed in more than 85% of AML cells (blasts) [5], and an increased level of CD33 has been correlated with poor survival [6].

PET and computed tomography (CT) is an important imaging modality used in nuclear medicine. PET has an advantage in providing physiological and biochemical information to identify normal versus malignant lesions, but lacks anatomical details. However, CT provides high-resolution images with substantial anatomical details but lacks physiological information. Therefore, in the past decades, the two imaging modalities have been integrated forming PET/CT, which provides accurate diagnosis with anatomical details which is crucial in biopsy and focal radiotherapy [7].

In relapsed/refractory AML patients who are undergoing hematopoietic stem cell transplantation (HSCT) with active disease, the current conditioning regime is often not sufficient for disease control. Increased radiation and chemotherapy may reduce the leukemia burden [8]; however, mortality from toxicities related to chemotherapy and high-dose total body irradiation (TBI) offsets any improvements in relapse rate [9]. In a recent study, leukemia-rich regions in the skeletal and lymphoid system were targeted using a CT-based image-guided precise radiation treatment modality (total marrow and lymphoid irradiation, TMLI) along with chemotherapy in the setting of HSCT. Although the treatment yielded progress reducing the relapse rate in high risk AML patients, the rate remained high [10]. The molecular imaging technique may help further target dose escalation to sites of high disease burden to enhance the therapeutic gain and limit doses to hematopoietic tissues and vital organs [11]. However, the feasibility and benefits of targeting CD33-positive avid leukemia with targeted radiation are unknown.

Described herein is an imaging method using an antibody conjugate such as 64Cu-DOTA-anti-CD33 immuno-PET- CT imaging for the detection of CD33+ AML cells in a mouse xenograft model. Besides detecting AML, unexpectedly, this imaging modality also provided information about the spatial distribution of disease in the whole body. Therefore, with a theranostic objective, the feasibility and efficacy of treating these CD33-avid high disease burden sites (representing spatial heterogeneity) using both PET and CT image-guided precision radiation treatment in the form of functional targeted marrow irradiation (fTMI) in combination with chemotherapy is demonstrated in this disclosure.

Disclosed herein is a non-invasive anti-CD33 immuno-PET-CT imaging method for the in vivo detection of AML disease with high sensitivity and specificity. Diagnostic and prognostic markers facilitate stratifying patients for treatment management. However, the current clinically approved diagnostic method is invasive, relying on single point (iliac crest) biopsies, which: 1) may not always be representative of the actual disease state, and 2) limits the number of times it may be performed. Therefore, in leukemia non-invasive PET-imaging using PET tracers including F18-FDG (metabolic activity) and F18-FLT (cell proliferation) have been tested for diagnosis and monitoring treatment response [11, 18-20]. Although FDG-PET has shown some success in diagnosing extramedullary disease in AML [21], it has also yielded highly inconsistent results because of changes in the metabolic activity of normal/tumor cells post treatment [22, 23]. Also, a recent study indicated that FLT-PET could identify the risk of early relapse in the spine prior to evidence of relapse by detection of minimal residual disease (MRD) [24]. However, these PET tracers are non-specific in that they detect metabolically active or highly proliferating cells, unlike CD33–PET imaging, which specifically detects cells expressing CD33, an accepted biomarker for AML. Therefore, CD33-based imaging can improve detection of AML with high specificity in the whole body. This approach can also provide a blueprint for selecting biopsy sites that would be greatly useful for early detection and longitudinal monitoring of treatment response.

As demonstrated in the working examples, the 64Cu-DOTA-anti-CD33 mAb PET was used to detect AML in vivo, showing very high specificity and sensitivity to CD33+ AML. The spatial information was achieved with whole body CT based 3D anatomical imaging. Notably, a spatial heterogeneity in the distribution of AML within the skeletal regions was observed, which would not be established with point biopsies. For example, CD33 activity was especially prominent in the L-spine and distal and proximal femurs, indicating a preferential niche for the disease at early stages. However, when the disease progressed, this spatial heterogenicity was reduced and the disease appeared to be more systemic. This finding suggests, contrary to previous beliefs, that leukemia may be initiated in multiple preferential niches, characterized by multifocal disease before becoming more systemic.

Several approaches involving CD33-targeted therapeutics have been developed for AML. Recently, a CD33 monoclonal antibody, (gemtuzumab ozogamicin [Mylotarg]) has been FDA-reapproved for AML immunotherapy. Although positive results have been reported from clinical trials of CD33-targeting drugs, dose limiting toxicities such as hepatotoxicities [25] during treatment are of concern.

Another novel application of functional imaging is the possibility to target these high disease burden sites with augmented doses of radiation (or dose painting) to enhance therapeutic gain. This strategy is exemplified in the clinical treatment planning simulation of fTMI using FLT-PET imaging [11] and suggests that high-disease burden areas (potentially leukemia niches) can be targeted with an elevated radiation dose, thus inflicting increased damage to disease sites while protecting the bulk of the marrow function and also preserving the functions of vital organs. However, dose escalation using TMI can also reach a limit (20 Gy), because of increasing dose exposure to vital organs. Additionally, it may also unnecessarily cause damage to the entire bone marrow. Thus, fTMI is expected to further advance TMI through molecular image-guided dose escalation to desired sites. The benefit of an fTMI treatment regimen will require pre-clinical validation. The disclosed novel preclinical fTMI modality using CD33 PET imaging and precision radiation delivery demonstrates the survival benefit of fTMI compared to conventional chemotherapy. High disease burden (CD33+ve) in these mice accounted for about 10-20% of the total skeletal volume. Therefore, localized radiation boosts to sites of high disease burden would enhance increased tumor cell killing without damaging the entire skeletal system. Therefore, fTMI facilitates preserving the majority of the bone marrow. Doses to the whole bone marrow are still required for successful treatment.

As the preclinical study was conducted using a murine anti-CD33 mAb, clone p67.6, for translational purposes, a new humanized anti-CD33 monoclonal antibody was generated for human imaging and treatment.

Thus, the human anti-CD33–PET-CT imaging modality disclosed herein can successfully detect AML in vivo, which can be used for diagnosis and monitoring treatment response in the whole body, including extramedullary disease. The molecular imaging method also detected heterogeneity in the spatial distribution of the AML, warranting caution in interpreting results from single-point biopsies. Furthermore, the therapeutic potential of this diagnostic imaging method was validated using a novel image-guided precision radiation treatment plan (fTMI). As a result, anti-CD33 PET-CT is a viable AML theranostic imaging method with translational potential.

Disclosed herein is a non-invasive PET-CT imaging method of detecting AML in vivo in a subject. The imaging method can be used for diagnosis and monitoring treatment response in the whole body, including extramedullary disease (MED). The imaging method also can be used to determine heterogenicity in the spatial distribution of the AML. The method comprises administering to a subject an effective dose of a radioactive isotope-labeled anti-CD33 antibody, exposing the subject to PET-CT scanning, and detecting CD33+ PET-CT signal in tissue or organ of the subject to determine the presence of the AML cancer cells. In some embodiments, the PET-CT scanning is carried out about 6 hours, about 12 hours, about 18 hours, about 24 hours, about 30 hours, about 36 hours, or about 48 hours after administration of the radioactive isotope-labeled anti-CD33 antibody. In some embodiments, the radioactive isotope-labeled anti-CD33 antibody is administered to the subject by intravenous injection. In some embodiments, the radioactive isotope is 64Cu. In some embodiments, the radioactive isotope is conjugated to the antibody via DOTA.

In another aspect, disclosed herein is a method of treating AML or EMD in a subject. The method comprises administering to a subject an effective dose of a radioactive isotope-labeled anti-CD33 antibody, exposing the subject to PET-CT scanning, detecting CD33+ PET-CT signal in tissue or organ of the subject to determine the presence of the cancer cells, and administering fTMI therapy to the subject based on the distribution of the CD33+ PET-CT signal, wherein the tissue or organ with a higher intensity of the CD33+ PET-CT signal receives a higher dose, a higher frequency, or a longer exposure of the fTMI therapy than the tissue or organ with a lower intensity of the CD33+ PET-CT signal. In some embodiments, the vital organs, or the tissue or organ having no CD33+ PET-CT signal does not receive any fTMI therapy. One or more treatment cycles of fTMI can be administered at a desired interval at the same dose or different doses. In some embodiments, the method further comprises administering to the subject a chemotherapy before or after the fTMI therapy. One or more chemotherapeutic agents for treating AML or EMD can be used. In some embodiments, the combination of the fTMI therapy and the chemotherapy results in a reduced dose, frequency, and/or intensity of the fTMI therapy or the chemotherapy comparing to each of the therapies used alone. In some embodiments, the chemotherapy is AraC. In some embodiments, the PET-CT scanning is carried out about 6 hours, about 12 hours, about 18 hours, about 24 hours, about 30 hours, about 36 hours, or about 48 hours after administration of the radioactive isotope-labeled anti-CD33 antibody. In some embodiments, the method further comprises transplanting bone marrow to the subject. In some embodiments, the radioactive isotope-labeled anti-CD33 antibody is administered to the subject by intravenous injection. In some embodiments, the radioactive isotope is 64Cu. In some embodiments, the radioactive isotope is conjugated to the antibody via DOTA.

In a related aspect, disclosed herein is a humanized anti-CD33 antibody suitable for the PET/CT imaging of a subject suffering from or at an elevated risk of suffering from AML. In some embodiments, the antibody is labeled by a radioactive isotope. In some embodiment, the antibody is 64Cu-DOTA-anti-CD33 antibody.

In an effort to improve theranostic, therapeutic efficacy and increase clinical relevance, a "humanized" anti-CD33 antibody was used for the current study. It is within the purview of one skilled in the art to make necessary modification of this antibody, for example, to facilitate the antibody conjugating to a suitable radioactive isotope such as 64Cu via 1,4,7,10-tetraazacyclododecane-1,4,7,10-tetraacetic acid (DOTA) without significantly lowering the binding affinity and specificity for CD33 and without significantly decreasing the ability to specifically target CD33-expressing cancer cells in vivo. In some embodiments, other radioactive isotopes can be used with or without a chelant agent. For example, 124I can be conjugated to the antibody without a chelant agent. Alternatively, 177Lu, 90Y and 225Ac can be conjugated to the antibody via DOTA for therapy, and 111In can be conjugated to the antibody via DOTA for imaging. In some embodiments, the modified humanized anti-CD33 antibodies or fragments thereof can be used as long as the binding affinity and specificity for CD33 in vivo are not significantly compromised. Thus, humanized antibodies and/or monoclonal antibodies can be used to maximize the specific binding and cancer imaging or detection.

As used herein, the term "antibody" refers to monoclonal antibodies, polyclonal antibodies, and antibody fragments prepared by recombinant nucleic acid techniques. The term may refer to an intact tetrameric immunoglobulin containing two complete light chains and two complete heavy chains, each with a variable region and a constant region. Alternatively, it may refer to a fragment thereof, such as an Fv fragment (containing only the variable regions of the light and heavy chains), an Fab fragment (containing the variable regions and some elements of the constant regions), a diabody, a single-chain antibody, or any other antibody fragment.

The term "humanized antibody" as used herein refers to an antibody containing structural elements of a human antibody (the acceptor) and the antigen binding site of a non-human antibody (the donor). "Humanized antibodies" contain a minimal number of residues from the non-human antibody. For instance, they may contain only the CDR regions of the non-human antibody, or only those residues that make up the hypervariable regions of the non-human antibody. They may also contain certain residues from outside the variable regions of the non-human polypeptide, such as residues that are necessary to mimic the structure of the non-human antibody or to minimize steric interference. In addition, humanized antibodies may contain residues that do not correspond to either the human or the non-human antibodies. The antibody conjugate disclosed herein such as the Cu-64 labeled, humanized anti-CD33 monoclonal antibody can be administered to a subject by subcutaneous, peritoneal, intravenous, intravascular, intramuscular, intradermal or transdermal injection, among other methods. In some embodiments, the radioactive isotope conjugated antibody can be administered by intravenous, subcutaneous or peritoneal administration. The 64Cu-DOTA-anti-CD33 antibody disclosed herein may be administered at a dose sufficient for detection by a scanning device.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1: Materials and Methods

Figure 2A:
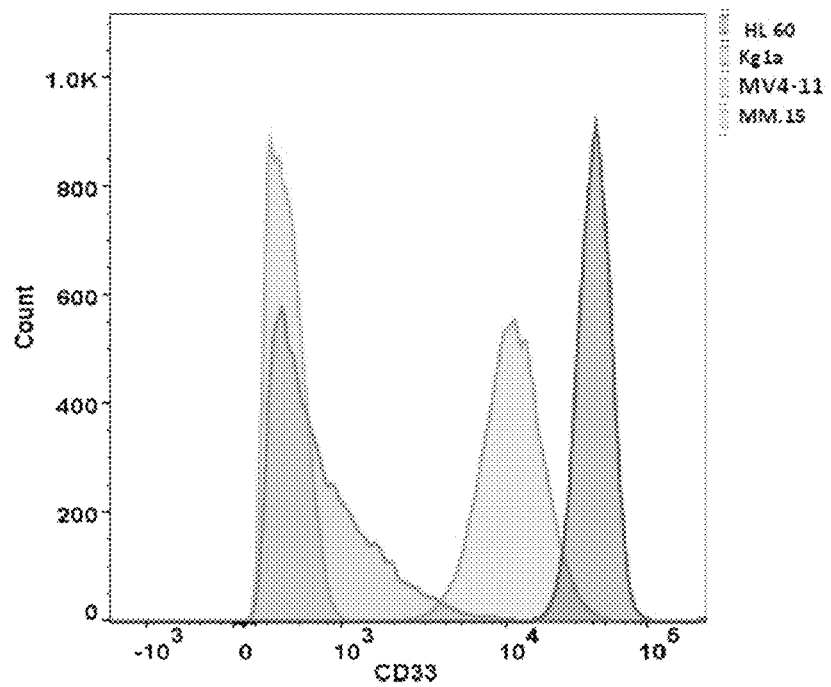
FIGS. 2A-2E show the anti-CD33-DOTA conjugated antibody immunoreactivity and quantification of CD33 antibody molecules per cell using BD QuantiBRITE PE.

Cell culture: Human AML cells (HL60, MV4-11, Kg1a), a murine AML cell line (MLL-Af9) and multiple myeloma (MM) cells MM.1S were used in this study and cultured using standard tissue culture condition. More specifically, human AML, MV4-11 cells, HL-60 cells, Kg1a and a murine AML cell line, MLL-AF9-GFP were obtained from Dr. Ching-Cheng Chen (City of Hope, Calif.). GFP-Luciferase positive (Gfp/Luc) MM.1S MM cells were provided by Dr. Xiuli Wang (City of Hope, Calif.). Parental cell lines were originally purchased from the American Tissue Culture Collection (U.S.A.). Human AML cell lines were cultured in IMDM medium; MLL-AF9 and MM cells were grown in RPMI-1640 medium. All media were supplemented with 10% fetal bovine serum. Cells were cultured at 5% CO2, 37° C. in a humidified incubator. MV4-11 and HL-60 cells were 100% positive for CD33 while Kg1a had <30% cells positive for CD33. Therefore, for further studies only MV4-11 and HL-60 AML cells were used (FIG. 2A).

Antibody: Murine anti-human CD33 clone p67.6 is an IgG1 kappa monoclonal antibody (mAb) that targets human CD33-positive cells of the myeloid lineage [12, 13]. The hybridoma was produced in a hollow fiber bioreactor and purified by Protein G and cation exchange chromatography. Anti-human CD33 PE (Clone WM 53) was obtained from BD Biosciences. Anti-human CD45 (clone: 2D1) was obtained from BioLegend, San Diego, Calif.

Humanized anti-CD33: The murine anti-CD33 M195 mAb was humanized by CDR grafting to reduce human anti-mouse antibody responses [14, 15]. The scFv was reformatted to a human IgG1 antibody by cDNA synthesis, transiently expressed in HEK293 cells and purified by Protein A chromatography.

The sequences for the light and heavy chains encoding huM195 (α-CD33) full-length mAb are shown below. The light chain contains the VL domain of huM195 fused to the kappa CL domain of M5A. The heavy chain contains the VH domain of huM195 fused to the constant heavy (CH1-3) domains of M5A.

huM195 (α-CD33) light chain (SEQ ID NO: 1) (the underlined sequence is the Kozak sequence and the sequence in bold and italic is the leader signal sequence):

CCGCCACC*ATGGAAACGACACACTGCTGCTGTGGGTGCTGCTT*

*TTGTGGGTGCCAGGCTCTACCGGC*GACATCCAGATGACACAGAGCCCT

TCTAGCCTGAGCGCCTCTGTGGGCGATAGAGTGACCATCACATGTAGAGC

CAGCGAGAGCGTGGACAACTACGGCATCAGCTTCATGAACTGGTTCCAGC

AGAAGCCCGGCAAGGCCCCTAAACTGCTGATCTACGCCGCCAGCAATCAA

GGCAGCGGAGTGCCTAGCAGATTTTCTGGCAGCGGCTCTGGCACCGACTT

CACCCTGACAATTAGCAGCCTGCAGCCTGACGACTTCGCCACCTACTACT

GCCAGCAGTCTAAAGAGGTGCCCTGGACCTTTGGACAGGGCACCAAGGTG

GAAATCAAGAGAACAGTGGCCGCTCCGAGCGTGTTCATCTTTCCACCAAG

CGACGAGCAGCTGAAAAGCGGAGCCGCTTCTGTCGTGTGCCTGCTGAACA

ACTTCTACCCCAGAGAAGCCAAGGTGCAGTGGAAGGTGGACAATGCCCTG

CAGAGCGGCAATAGCCAAGAGAGCGTGACCGAGCAGGACAGCAAGGATAG

CACATACAGCCTGAGCAGCACACTGACCCTGAGCAAGGCCGACTACGAGA

AGCACAAAGTGTACGCCTGCGAAGTGACACACCAGGGCCTGTCTAGCCCT

GTGACCAAGAGCTTCAACCGGGGCGAGTGTTGA huM195 (α-CD33) heavy chain (SEQ ID NO: 2) (the underlined sequence is the Kozak sequence and the sequence in bold and italic is the signal sequence):

GCCGCCACC*ATGAAGTGCAGCTGGGTCATCTTCTTTC TGATGGCC*

*GTGGTCAC*CGGCGTGAACTCTCAGGTTCAACTGGTGCAGTCTGGCGCCG

AAGTGAAGAAACCTGGCAGCTCTGTGAAGGTGTCCTGCAAGGCCAGCGGC

TACACCTTTACCGACTACAACATGCACTGGGTCCGACAGGCTCCAGGACA

GGGACTCGAGTGGATCGGCTACATCTACCCTTACAATGGCGGCACCGGCT

ACAACCAGAAGTTCAAGAGCAAGGCCACCATCACCGCCGACGAGAGCACA

AACACAGCCTACATGGAACTGAGCAGCCTGAGAAGCGAGGACACCGCCGT

GTACTATTGTGCCAGAGGCAGACCCGCCATGGATTATTGGGGACAGGGCA

CCCTGGTTACCGTGTCTAGCGCCTCTACAAAGGGCCCTAGTGTGTTCCCT

CTGGCTCCTAGCAGCAAGAGCACATCTGGTGGAACAGCCGCTCTGGGCTG

CCTGGTCAAGGATTACTTTCCTGAGCCTGTGACCGTGTCCTGGAATAGCG

GAGCACTGACAAGCGGCGTGCACACATTTCCAGCTGTGCTGCAGAGCAGC

GGCCTGTACTCTCTGTCTAGCGTGGTCACAGTGCCTAGCTCTAGCCTGGG

CACCCAGACCTACATCTGCAACGTGAACCACAAGCCTAGCAACACCAAGG

TGGACAAGAAGGTGGAACCCAAGAGCTGCGACAAGACCCACACCTGTCCT

CCATGTCCTGCTCCAGAACTGCTCGGCGGACCCTCCGTTTTCCTGTTTCC

ACCTAAGCCTAAGGACACCCTGATGATCAGCAGAACCCCTGAAGTGACCT

GCGTGGTGGTGGATGTGTCCCACGAGGACCCAGAAGTGAAGTTCAATTGG

TACGTGGACGGCGTGGAAGTGCACAACGCCAAGACCAAGCCTAGAGAGGA

ACAGTACAACAGCACCTACAGAGTGGTGTCCGTGCTGACCGTGCTGCACC

AGGATTGGCTGAACGGCAAAGAGTACAAGTGCAAGGTGTCCAACAAGGCT

CTGCCCGCTCCTATCGAGAAAACCATCTCCAAGGCCAAGGGCCAGCCAAG

AGAACCCCAGGTTTACACACTGCCTCCAAGCAGGGACGAGCTGACCAAGA

ATCAGGTGTCCCTGACCTGCCTCGTGAAGGGCTTCTACCCTTCCGATATC

GCCGTGGAATGGGAGAGCAATGGACAGCCCGAGAACAACTACAAGACAAC

CCCTCCTGTGCTGGACAGCGACGGCTCATTCTTCCTGTACAGCAAGCTGA

CAGTGGACAAGTCCAGATGGCAGCAGGGCAACGTGTTCAGCTGTTCTGTG

ATGCACGAGGCCCTGCACAACCACTACACCCAGAAAAGCCTGTCTCTGAG

CCCCGGCAAATGA

Anti-human CD33 antibody DOTA and $^{64}$Cu conjugation: The mouse and humanized anti-human CD33 mAb were conjugated with the metal chelator 1,4,7,10-tetraazacyclododecane-N,N',N'',N'''-tetraacetic acid (NHS-DOTA; Macrocyclics, Dallas, Tex.) as previously described [16]. Briefly, 5 mg of antibody was buffer exchanged into sodium bicarbonate buffer, conjugated to NHS-DOTA, (DOTA:mAb molar ratio of 30:1, 1 hour at room temperature), buffer exchanged into 0.25 M ammonium acetate pH 7.0, and concentrated to >5 mg/ml.

Anti-CD33-DOTA mAb was radiolabeled with $^{64}$Cu (Mallinckrodt Institute of Radiology, Washington University School of Medicine) at a specific activity of 10 μCi/mg in 0.25 M NH$_4$OAc, pH 5.0 for 45 min at 43° C., chased with 1 mM diethylenetriamine pentaacetic acid (DTPA), following which the $^{64}$Cu-DOTA-anti-CD33 conjugate was purified on a size-exclusion Superdex-200 preparative column (GE Healthcare Life Sciences).

The anti-human CD33 mAb, DOTA-anti-human CD33 mAb and DOTA-anti-human CD33 mAb vialed product were analyzed by SDS-PAGE (4-12% gradient polyacrylamide) and isoelectric focusing, and the gels were stained with Coomassie Brilliant Blue for visualization.

Flow cytometry: Flow cytometry was used to analyze CD33 and CD45 expression in human AML (MV4-11, HL 60 and Kg1a) and multiple myeloma cells (MM1S) using mouse anti-human CD33 and CD45 antibodies. Staining and flow cytometry analysis was performed as per standard protocols. Data were acquired from a BD Fortessa cytometer and analyzed in FlowJo V 10.0 software.

Anti-CD33-DOTA immunoreactivity: All radiolabeled antibodies were analyzed for immunoreactivity to soluble CD33 by a liquid phase assay incubating the radiolabeled protein with 20 equivalents by the mass of purified CD33 at 37° C. for 15 min. The resultant solution was analyzed by HPLC-SEC using a Superose 6 10/300 GL column (GE Healthcare). Anti-CD33 immunoreactivity was determined by integrating the area on the HPLC radiochromatogram and calculating the percentage of radioactivity shifting to higher molecular weights, consistent with binding to CD33 Fc antibody (67-85 kDa).

Stability Studies: Protein stability studies were performed on $^{64}$Cu DOTA-anti-CD33 incubated in fresh mouse serum at 37° C. Aliquots were analyzed on an HPLC SEC Superose 6 column at 4 hours, 24 hours and 48 hours, respectively.

Dylight-488 conjugation of Clone P67.6: The P67.6 antibody was conjugated to Dylight-488 as per manufacturer's protocol (Abcam Dylight® 488 Fast Conjugation Kit (ab201799). Briefly, to 100 μg of antibody (in 100 μl) 10 μl of modifier reagent (1 μl/10 μl antibody mix, [1:10 v/v]) was added. The mixture was then added to Dylight-488 conjugation reagent and incubated for 15 min in the dark. The reaction as stopped by adding 10 μL (1 μl/10 μl antibody mix, (1:10 v/v)) of quenching reagent.

CD33 expression: The cell surface expression of CD33 on AML cells and multiple myeloma cells was determined using BD QuantiBRITE PE system as per the manufacturer's instruction. Briefly, $1\times10^6$ cells were stained with PE-conjugated anti-CD33 MoAb (BD Biosciences) and 20,000 events were acquired for each sample using BD Fortessa cytometer, and data were analyzed using FlowJo V10.0. The BD QuantiBRITE PE contains four sets of beads with PE-molecules covalently attached to beads at four different levels. Geometric means (MFI) of all four beads were determined and using lot-specific values for the PE molecules per bead (provided in each BD Quantibrite PE kit box) log 10 for geometric mean (MFI) and for the PE-molecules per bead was calculated. Then, a linear regression was plotted for log 10 PE molecules per beads against Log 10 geometric mean using y=mx+c equation, where y equals Log 10 geometric mean and x equals Log 10 PE molecules per bead. The CD33 molecules per cell on AML cells were determined by substituting the Log geometric means (y) in the equation and solved for Log PE molecules per cell (x). Anti-log of x resulted in the total number of CD33 molecules per cell.

Lentivirus preparation and transduction into MV4-11 cell line: MI-Luciferase-IRES-mCherry was a gift from Xiaoping Sun (Addgene plasmid #75020) [26]. MI-Luciferase-IRES-mCherry plasm id (10 μg) co-expressing mCherry and luciferase along with VSVG envelope and CMV packaging vectors were transfected into HEK293T cells, and supernatant was collected at 72 hours. The supernatant containing viral particles was mixed with 5× PEG (SBI system Biosystems, Palo Alto, Calif.) and kept overnight at 4° C. in the rotor. The next day, the supernatant was centrifuged at 2000 rpm for 10 minutes to collect viral particles in a pellet, which was re-suspended into serum free X-VIVO™ 10 media (Lonza) and stored at −80° C. until further use. The titer of the viral particles was quantified using transducing HEK cells. The MV4-11 cells were transduced with 10 μl of viral particles in a 96-well plate in the presence of 8 μg/ml polybrene and centrifuged at 1600 rpm for 60 minutes at room temperature on the first day and the second day. The transduced MV4-11 cells were transferred into fresh IMDM media at 48 hours and allowed to expand for another 1-2 days. The transduced mCherry-positive cells were sorted on a BD FACSAria III (BD Biosciences) flow-cytometry sorter and used for in-vitro luciferase expression validation and in-vivo transplantation experiments.

Bioluminescence imaging (BLI) of Leukemia cells in vivo: For non-invasive assessment of leukemic burden, whole body imaging was performed every week using the LagoX Imaging System (Spectral Imaging, Tucson, Ariz.). Mice were injected with D-Luciferin solution (i.p. 150 mg/kg), and 5 minutes later the mice were anesthetized with isoflurane (Faulding Pharmaceuticals) and imaged. Supine, prone and side view images were acquired for 10-30 seconds and using AMIView software the photon emission transmitted from mice was captured and quantitated in photons/$sec/^{cm2}$/sr. Further analysis of the images was done using Aura 2.0.1 software.

Diagnostic accuracy: Sensitivity was calculated by taking the ratio of CD33+ AML mice that had a percent ID/g above a given threshold, to the total number of CD33+ mice. Specificity was calculated by taking the ratio of CD33− mice that had a percent ID/g below the same threshold to the total number of CD33− mice. The diagnosis percent ID/g threshold was set at 2.75% for biodistribution data of whole left femur. All Mice in AML group (both MV4-11 and HL-60) were considered positive for CD33+ leukemia if they contained CD33+ cells in the left femoral bone marrow as determined by flow cytometry.

microPET-CT imaging and biodistribution studies: Mice bearing CD33-positive AML cells (MV4-11, HL-60), CD33-negative MM cells (MM1S) or non-leukemic control mice were injected IV with $^{64}$Cu-DOTA-anti-CD33 (100 μCi/10 μg), or $^{64}$Cu-DOTA-anti-CD33 (100 μCi/10 μg)+500 μg of unlabeled anti-CD33-DOTA (1:50). Each group consisted of at least 5 mice; representative data for each group are presented. Static PET scans were acquired at 1 day (40 minutes scan), and 2 days (60 minutes scan, with whole body CT at 100 μm resolution) post-injection using InVeon PET/CT (Siemens). For biodistribution studies, mice were euthanized at 24 hours and/or 48 hours, both time points showed activity. Various organs were obtained from control and AML leukemia-bearing mice. Wet weights of each organ were determined, and radioactive counts from each tissue/organ were measured using a WIZARD2 automatic gamma counter (PerkinElmer). Biodistribution and imaged PET activity of $^{64}$Cu-DOTA-anti-CD33 was presented as the percent injected dose per gram or organ/tissue (% ID/g). MV4-11 with cold-CD33 block and CD33-MM1S served as negative controls. Post Processed PET image analysis was performed by Vivoquant (Invicro).

Molecular image-guided radiation treatment with functional TMI: Briefly, a cone beam CT (CBCT) of an irradiator was used to acquire whole body mouse CT imaging. This CT image was then combined with CD33 based PET-CT images to contour/define regions of high levels of leukemia activity (PET signal greater than 10% ID/g was considered regions of high activity). Three-dimensional (3D) dose calculations were performed using the SmART-treatment plan [17]. The fTMI was performed in three steps: First, the TMI treatment plan was calculated based on whole body CT scanning targeting the entire skeletal system and other disease sites (e.g., spleen) while sparing vital organs (lungs, liver, kidney, intestine). Second, regions with high activity were selected for further dose escalation (boost) and then combined with two treatment plans to develop fTMI. Third, planned fTMI was delivered under anesthesia, and target positions were verified using 3D CT scanning prior to radiation delivery. The NSG mice received TMI (2 Gy) and boost radiation (2 Gy) to regions with high CD33 PET activity including joints in the femur, tibia, and humerus, and spleen and lumber spine, followed by 2 days of AraC (40 mg/kg) and 24 hours later with $2\times10^6$ bone marrow (BM) cells for transplantation. Dose escalation was limited in radiosensitive NSG mice (Myeloablative dose ~4 Gy) since fTMI (4Gy TMI+2 Gy Boost) was lethal even after a BM transplant (BMT, data not shown). Therefore, fTMI along with chemotherapy was tested in a more radio-resistant and immune-competent B6 mouse (~11 Gy myeloablative) model of AML (MLL-AF9). The boost regions were extrapolated from our NSG model. fTMI (6 Gy TMI+3 Gy boost) was delivered in 2 fractions 6 hours apart, followed by 2 days of AraC (40 mg/kg) and then BM cells (2×106 cells) for transplantation. Mean survival (in days) was calculated for fTMI+AraC treated mice, untreated AML mice or mice treated with AraC alone (100 mg/kg IP, 3 consecutive days and BMT). Disease in NSG mice was monitored post treatment every week using BLI until the mice were moribund and euthanized. Disease in the B6 model was determined using flow cytometry for GFP+ MLL-AF9 in peripheral blood.

Mouse AML models: immunodeficient (NSG) and immunocompetent (B6): All animal experiments were carried out in accordance to the guidelines of Institutional Animal Care and Use Committee (IACUC). The NSG (NOD-scidIL2Rg$^{null}$) mice were purchased from the Jackson Laboratory and were in bred in City of Hope animal breeding facility. The NSG mice were treated with 2-2.5 Gy radiation 24 hours before transplant as a preconditioning regime to ensure faster engraftment. Human AML and MM cells ($2\times10^6$ cells) were injected via tail vein, and engraftment was determined using bioluminescent imaging (BLI) 7-10 days post-transplant. Biodistribution and $^{64}$Cu-DOTA-anti-CD33 mAb imaging studies, chemotherapy and radiation interventions were performed around 14-21 days post-transplant. For an immunocompetent model, MLL-AF9-GFP, a murine AML cell line ($2\times10^6$ cells) was injected via tail vein without any precondition radiation, and engraftment was determined using flow cytometry for GFP+MLL-AF9 in peripheral blood. Chemotherapy and radiation interventions were performed around 7 days post transplant.

Statistical analysis: Statistical analysis was performed using ANOVA and the two-tailed students-t test. The Pearsons correlation coefficients were calculated assuming a Gaussian distribution. The difference was considered significant when the p value was <0.05. The Kaplan-Meier survival curve and all other graphs were generated using GraphPad Prism Software V 7.2.

Example 2: Generation of $^{64}$Cu-DOTA Anti-CD33 (p67.6) Monoclonal Antibody

This example demonstrates successful production of $^{64}$Cu-DOTA-anti-CD33 monoclonal antibody.

Figure 1B:
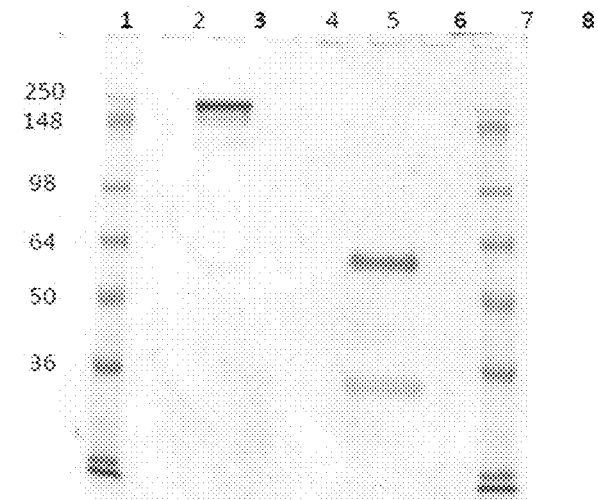
Figure 1C:
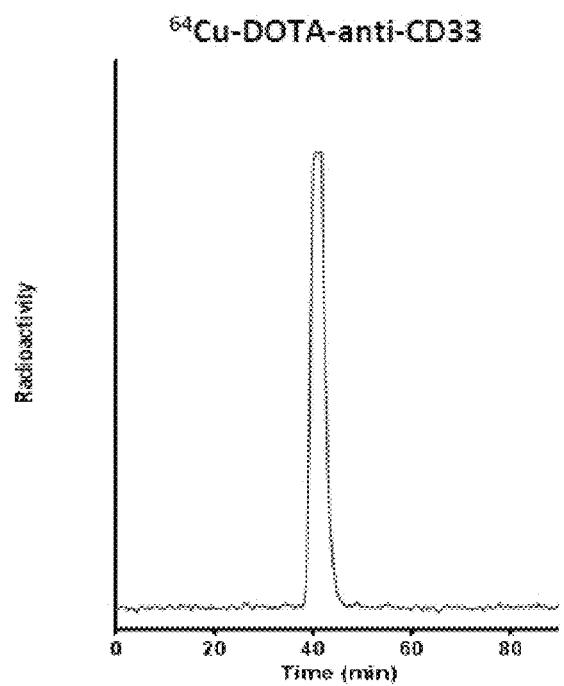
Figure 1D:
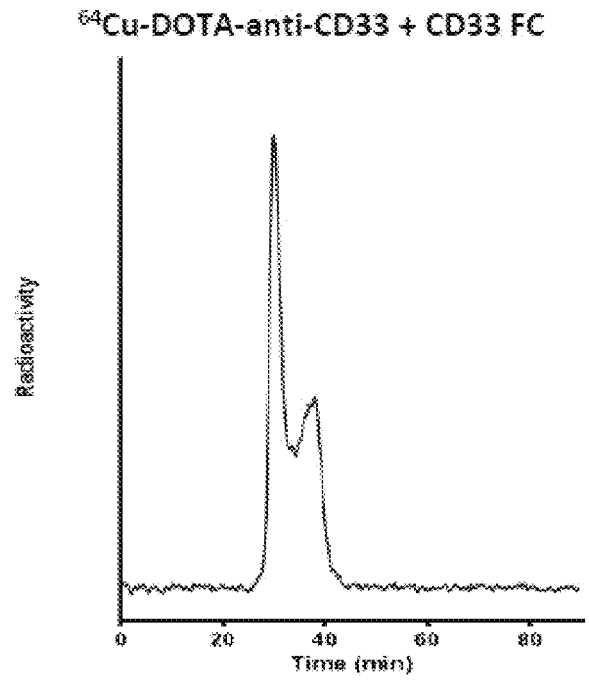

For use as an immunoPET tracer, the anti-human CD33 mAb, mouse hybridoma P67.7, was produced, purified, conjugated to the metal chelate DOTA and radiolabeled with $^{64}$Cu. Coomassie stained SDS-PAGE gel electrophoresed under reducing conditions shows the purity, with 2 bands corresponding to the light and heavy chains (FIG. 1A). Post-DOTA conjugation, iso-electrofocusing gel analysis shows a shift to a more acidic pH, confirming the conjugation process (FIG. 1B). The radiolabeled $^{64}$Cu-DOTA-anti-CD33 mAb was analyzed by size exclusion chromatography (SEC) and the radiochromatogram showed a single peak, with a retention time corresponding to a mAb (FIG. 1C). The immunoreactivity of DOTA-anti-CD33 mAb was evaluated by incubating the $^{64}$Cu-DOTA-anti-CD33 with soluble CD33-Fc antigen and analyzed by SEC. The radiochromatogram showed a faster retention time (~30 minutes), indicating an increase in molecular size consistent with binding to CD33 Fc soluble antigen (67-85 kDa) (FIGS. 1D, 1E). The $^{64}$Cu-DOTA-anti-CD33 mAb was shown to be stable in serum both in vitro and in vivo for 48 hours (FIGS. 1F, 1G).

Example 3: CD33 Cell Surface Expression in AML Cells

This example demonstrates that the $^{64}$Cu-DOTA-anti-CD33 antibody showed immunoreactivity to CD33-positive AML cell lines.

Figure 2B:
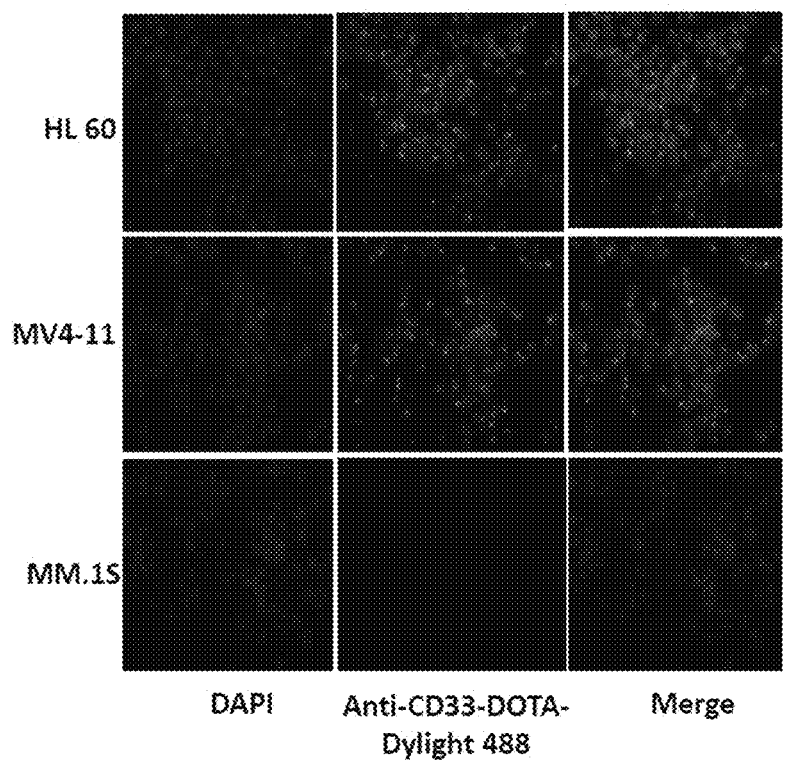
Figure 2C:
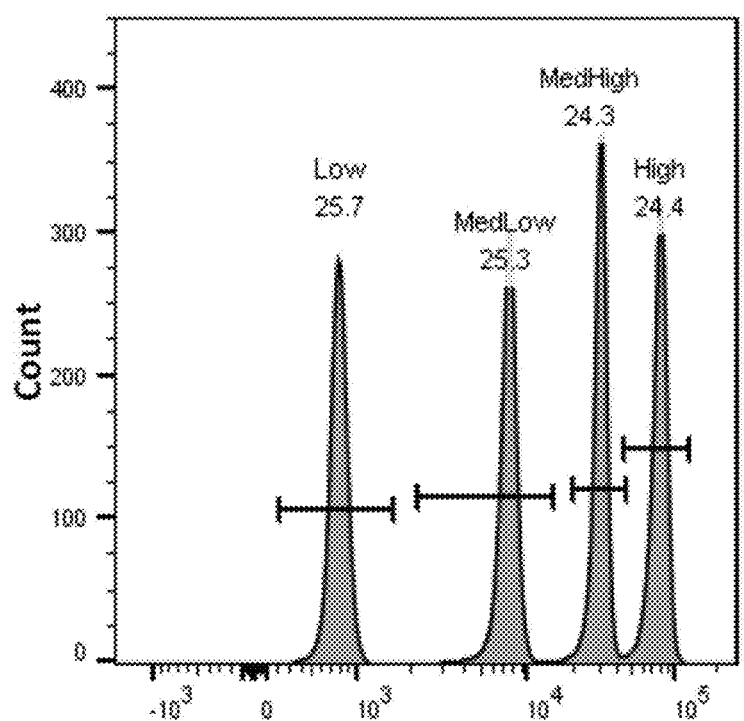
Figure 2D:
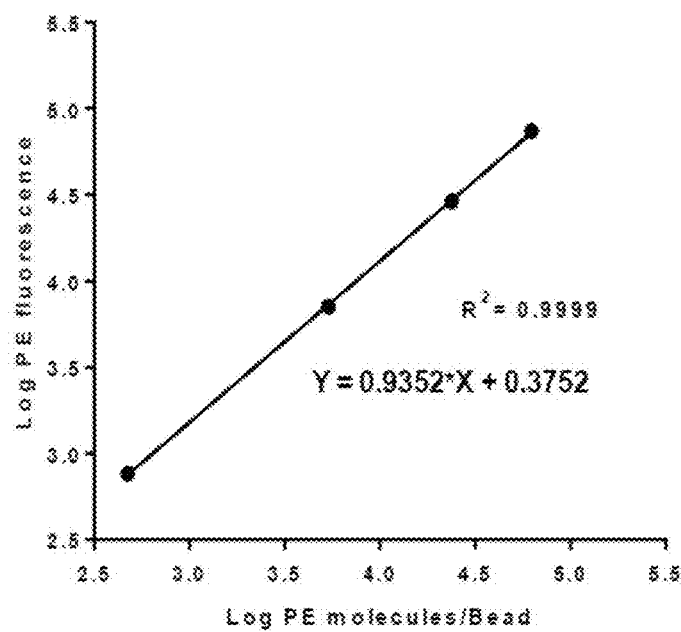
Figure 2E:
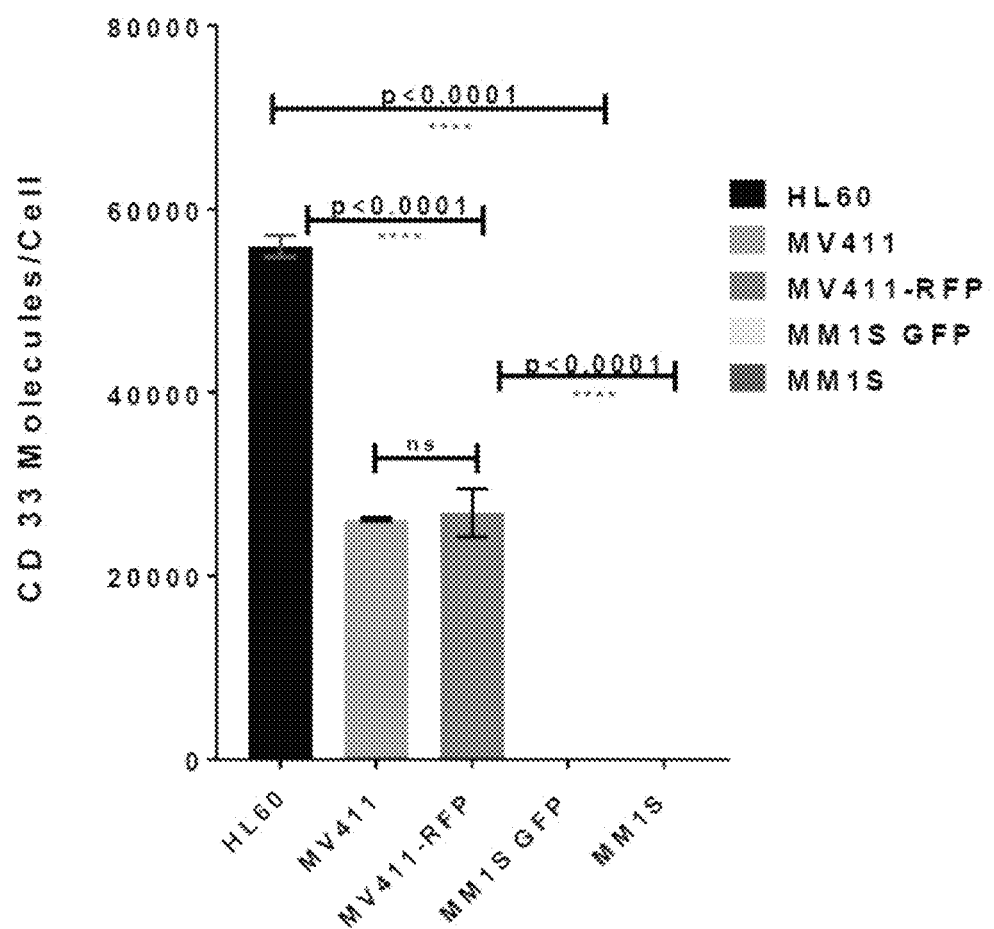

The murine DOTA-anti-CD33 mAb was tested for binding and specificity by flow cytometry using CD33 positive MV4-11, HL-60 cells, Kg1a, and the CD33-negative MM.1S-GFP cells. The $^{64}$Cu-DOTA-anti-CD33 antibody showed immunoreactivity towards CD33-positive AML cell lines but not in CD33-negative MM.1S cells (FIG. 2A). The immunoreactivity of the antibody was further confirmed by immunofluorescence: HL60 cells showed brighter staining than MV4-11, whereas negative control MM.1S showed no staining (FIG. 2B). The total number of CD33 cell surface receptors per cell was determined using the BD Quantibrite PE kit (FIGS. 2C, 2D). The HL-60 AML cell line expressed ~55,000 cell surface CD33/cell, versus ~26,000/cell in MV4-11 (FIG. 2E).

Example 4: PET-CT Imaging and Biodistribution of CD33+ AML Cells in Mouse Model

This example demonstrates biodistribution of $^{64}$Cu-DOTA-anti-CD33 antibody in AML bearing mice.

Figure 3D:
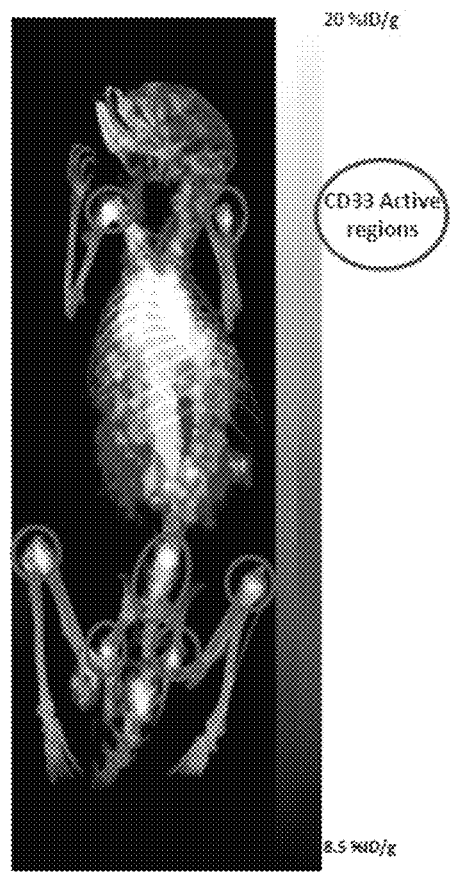
Figure 3F:
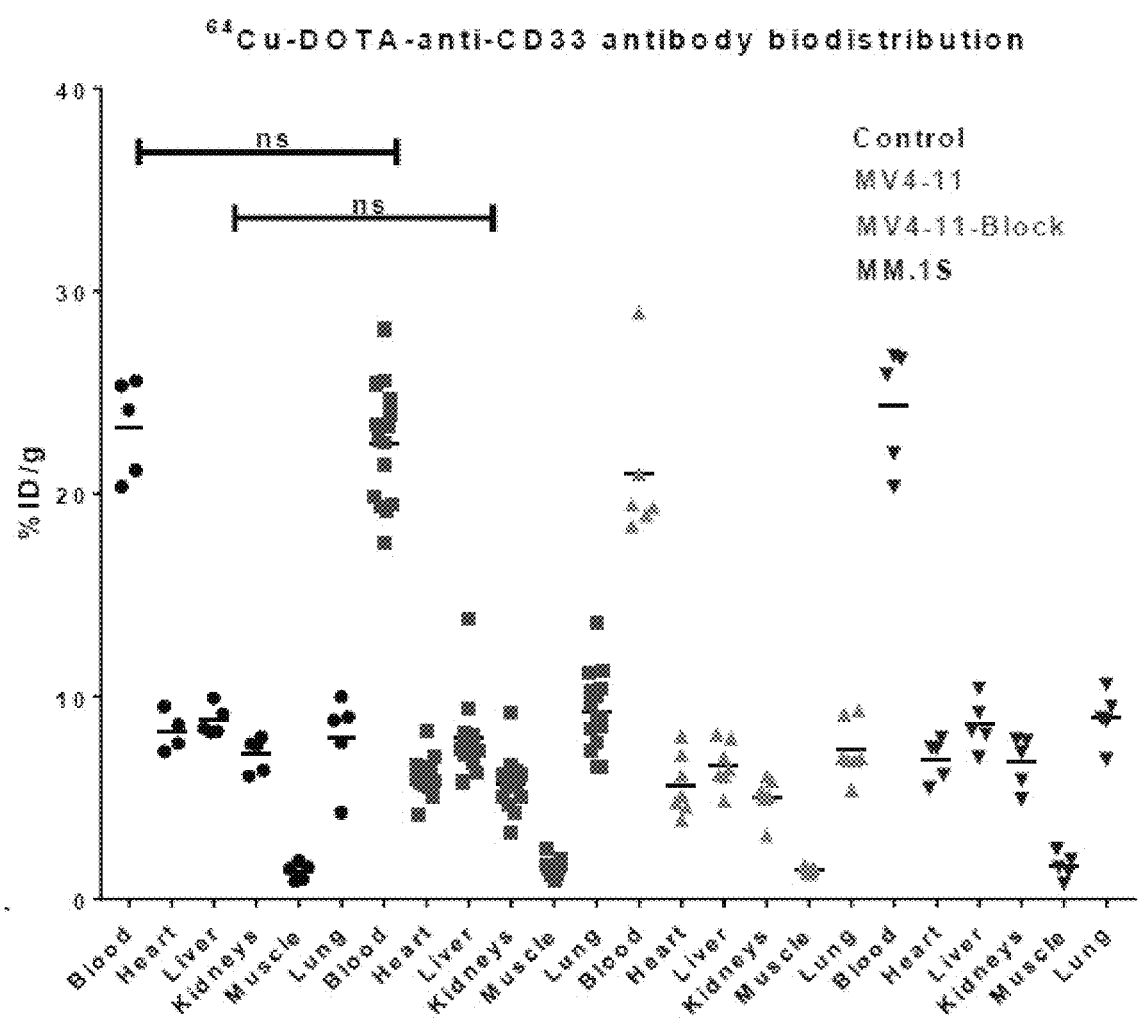

$^{64}$Cu-DOTA-anti-CD33 mAb immuno PET-CT in vivo imaging was performed in NSG mice bearing CD33+ AML cells, CD33-MM cells, and non-leukemic control mice. Mice were injected with $^{64}$Cu-DOTA-anti-CD33 mAb (100 µCi/10 µg) 24-48 hours prior to PET imaging. As an additional control for specificity, the $^{64}$Cu-DOTA-anti-CD33 mAb (100 µCi/10 µg)+500 µg of unlabeled DOTA-anti-CD33-mAb (1:50) were injected into mice bearing CD33+ AML cells. Bioluminescent imaging of AML and MM.1S cells in NSG mice was carried out 24 hours prior to $^{64}$Cu-DOTA-anti-CD33 mAb injections. The engraftment of AML and MM cells was also measured in the femur, L-spine, and spleen using FACS upon harvesting tissues/organs after imaging and biodistribution studies. PET-CT images (sagittal and coronal) clearly show CD33+ activity only in MV4-11 AML mice, but not in mice given cold CD33, mice with MM.1S, and non-leukemic control mice (FIGS. 3A, 3B). CD33+ PET activity was detected in the femur, tibia, and humerus joints; L-spine; and pelvic bone in CD33+ MV4-11-bearing mice and is highlighted in FIG. 3D. Although BLI and flow cytometry indicated high levels of myeloma cells in MM.1S bearing mice, there was no detectable CD33+ activity; similarly, the mice injected with cold unlabeled CD33 antibody showed no CD33+ PET signal, suggesting high specificity (FIGS. 3A-3C).

Figure 4A:
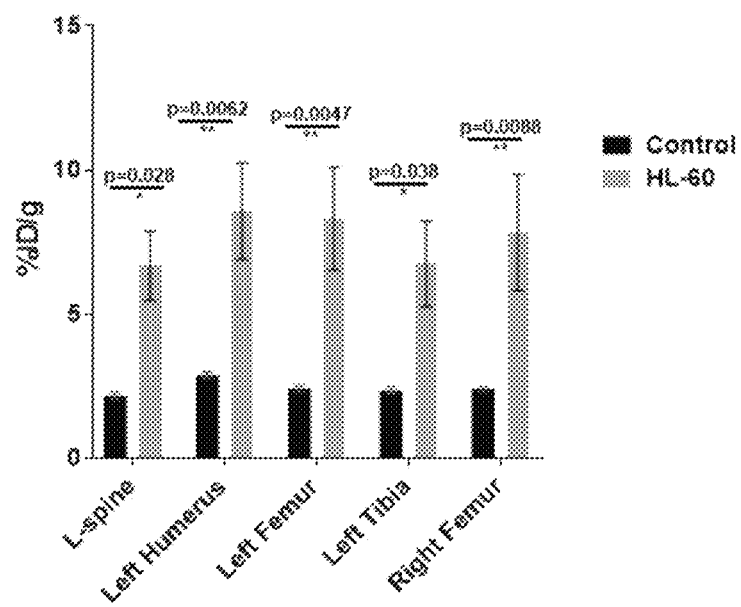
FIGS. 4A-4B show bio-distribution of 64Cu-DOTA-anti-CD33 antibody in HL-60 AML and control (no leukemia) mice. Biodistribution of 64Cu-DOTA-anti-CD33 in bones (FIG. 4A) and different tissues (FIG. 4B) was conducted 48 hours post injection. Plot of % ID/g of different tissues has been shown in the figure and evidently the CD33 activity was significantly high in bones of HL-60 AML mice in comparison to no leukemia control mice. The % ID/g between groups was slightly significant for blood and lung whereas heart, liver, stomach, small and large intestine and kidney were not significant. Statistical significance was determined using ANOVA and multiple "t" test and considered significant when P<0.05.
Figure 4B:
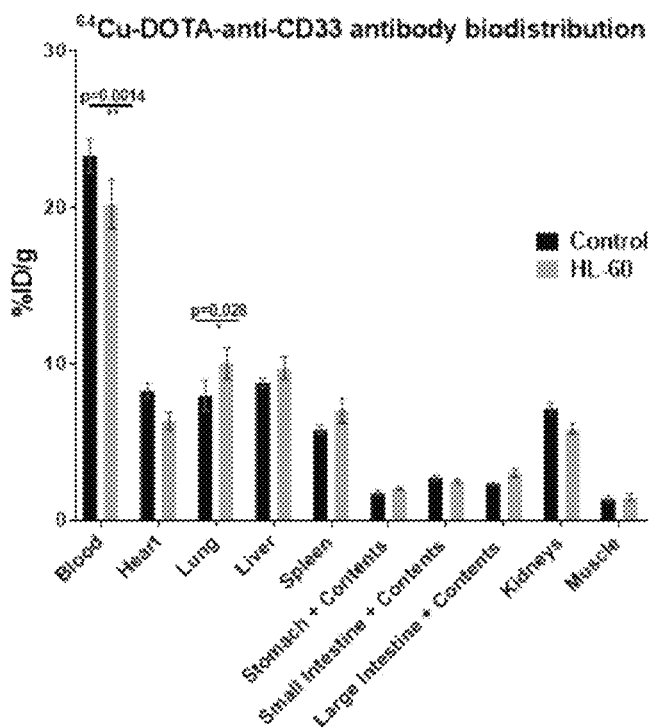
Figure 5A:
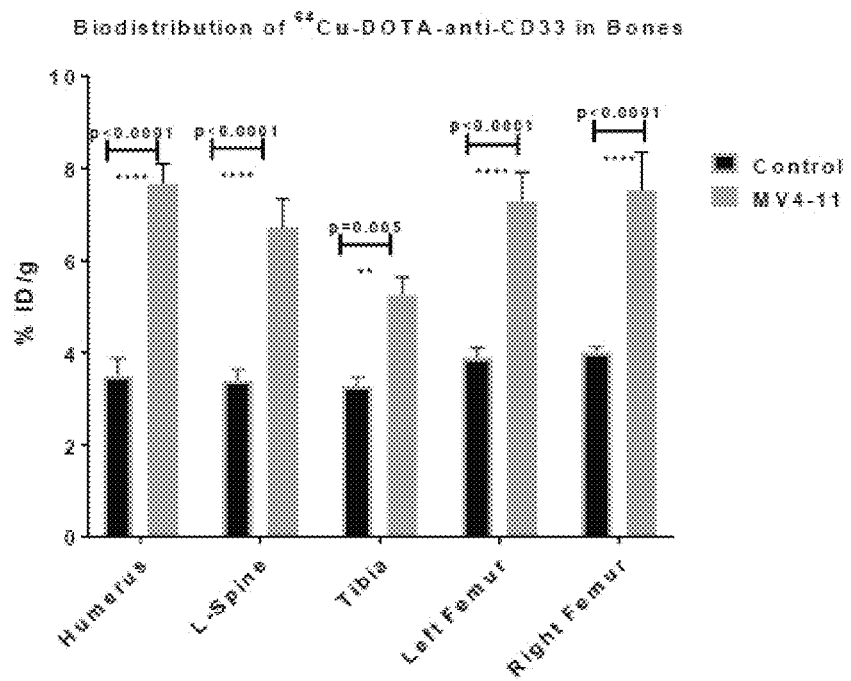
FIGS. 5A-5B show biodistribution of 64Cu-DOTA-anti-CD33 in bones (FIG. 5A) and different tissues (FIG. 5B) observed 24 hours/48 hours post injection.
Figure 5B:
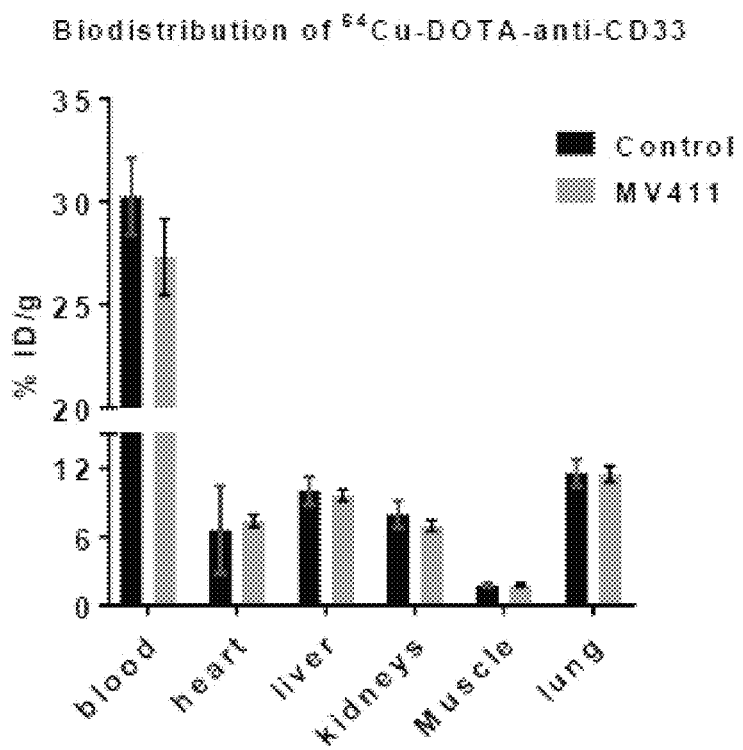

Biodistribution studies were carried out in mice from respective groups by harvesting different organs/tissues 24-48 hours post injection of the $^{64}$Cu-DOTA-anti-CD33 mAb, and the activity was measured using a gamma counter. The % ID/g of tissues/organs was plotted to determine the activity. The PET-signal was similar in all groups for blood, liver, lung, intestine and kidney (FIG. 3E). However, the % ID/g was particularly high in bones and spleen (hematological tissues) in CD33+ bearing MV4-11 AML mice, but not in CD33-MM mice, cold-blocked AML mice, or control non-leukemic mice (FIG. 3D). $^{64}$Cu-DOTA-anti-CD33 targeting was validated independently using a second AML cell line, HL-60, and similar biodistribution results were obtained (FIGS. 4A, 4B). The MV4-11 AML mice had CD33+ activity in the femur, tibia, L spine, and humerus (FIGS. 5A, 5B).

Figure 6A:
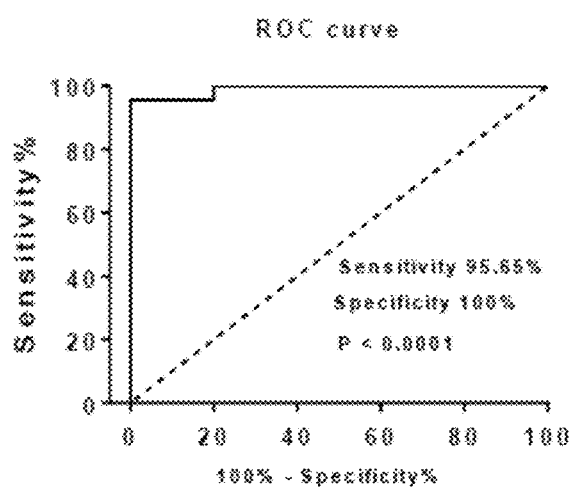
FIGS. 6A-6D show the sensitivity and specificity of anti-CD33 imaging method and correlation with leukemia engraftment. Sensitivity and specificity were calculated as described in Example 1.

The sensitivity and specificity were calculated from biodistribution of the $^{64}$Cu-DOTA-anti-CD33 mAb injected AML mice. The ROC curves showing sensitivity vs 100-specificity for biodistribution data from the femur show high sensitivity (~95%) and specificity (100%) (FIG. 6A).

Figure 6B:
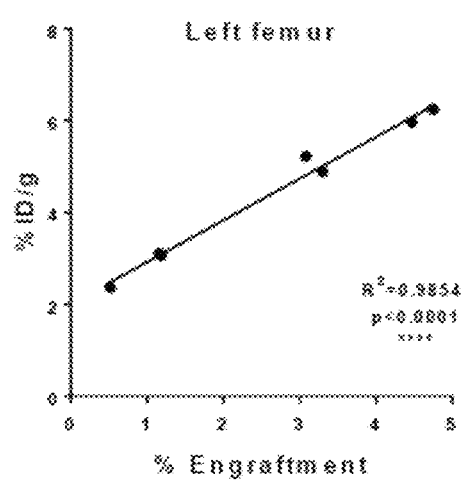
Figure 6C:
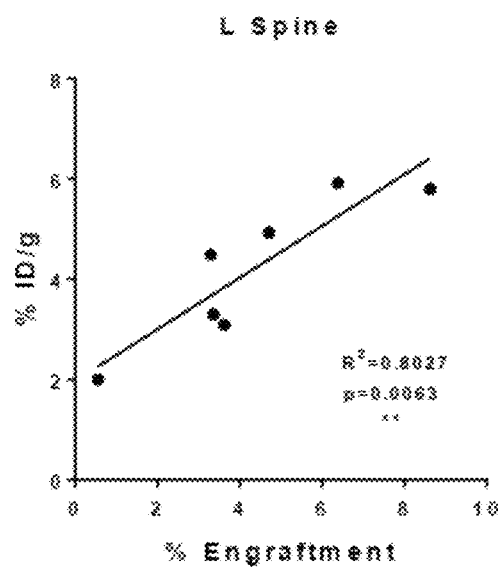
Figure 6D:
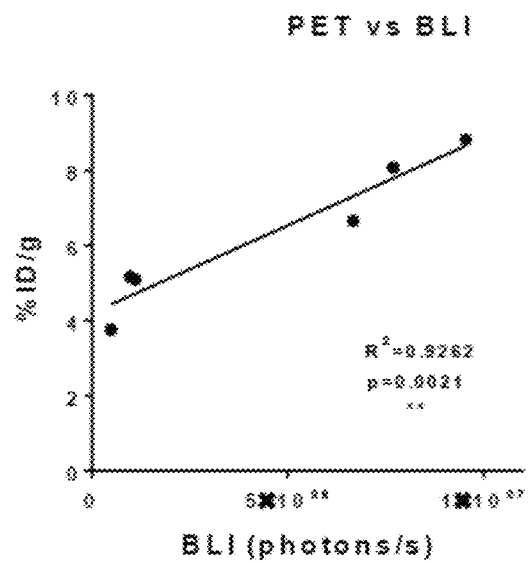

Further, the femur and L-spine of AML bearing mice were contoured in PET-CT images. The extent of engraftment from these bones was then determined by flow cytometry of human CD45+ cells/MV4-11-RFP. A high correlation was observed between PET-CT signals and percent engraftment (R2 value for femur and L-spine is 0.9854 and 0.8027, respectively) (FIGS. 6B, 6C). Additionally, the femur of AML bearing mice was contoured both in BLI and PET-CT images, and a high correlation was observed between BLI and PET-CT signals (R2=0.9262) (FIG. 6D). However, spatial localization was evident in PET-CT in comparison to BLI images, which were diffuse.

Example 5: Spatial Heterogeneity in AML In Vivo

This example demonstrates the localization pattern of AML using the anti-CD33 PET/CT imaging technique.

Figure 7A:
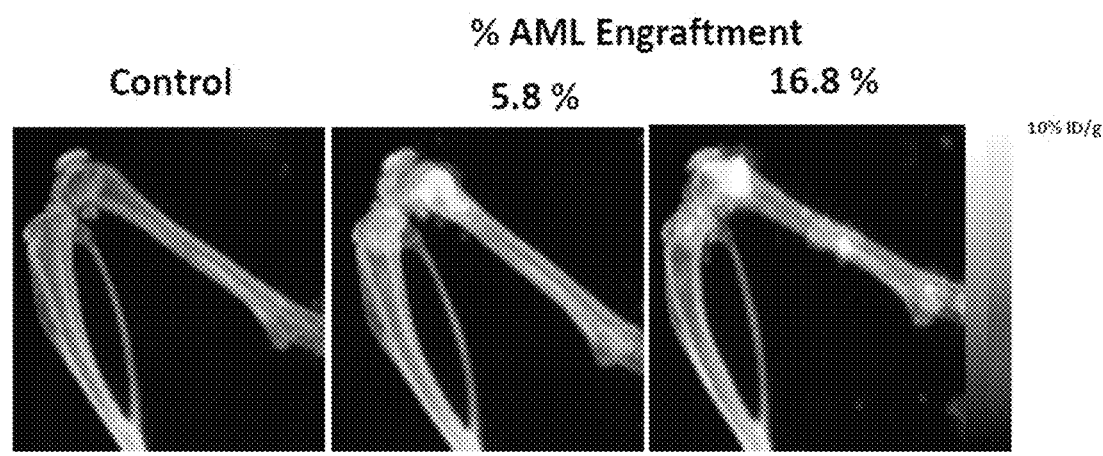
FIGS. 7A-7B show spatial distribution of AML.
Figure 7B:
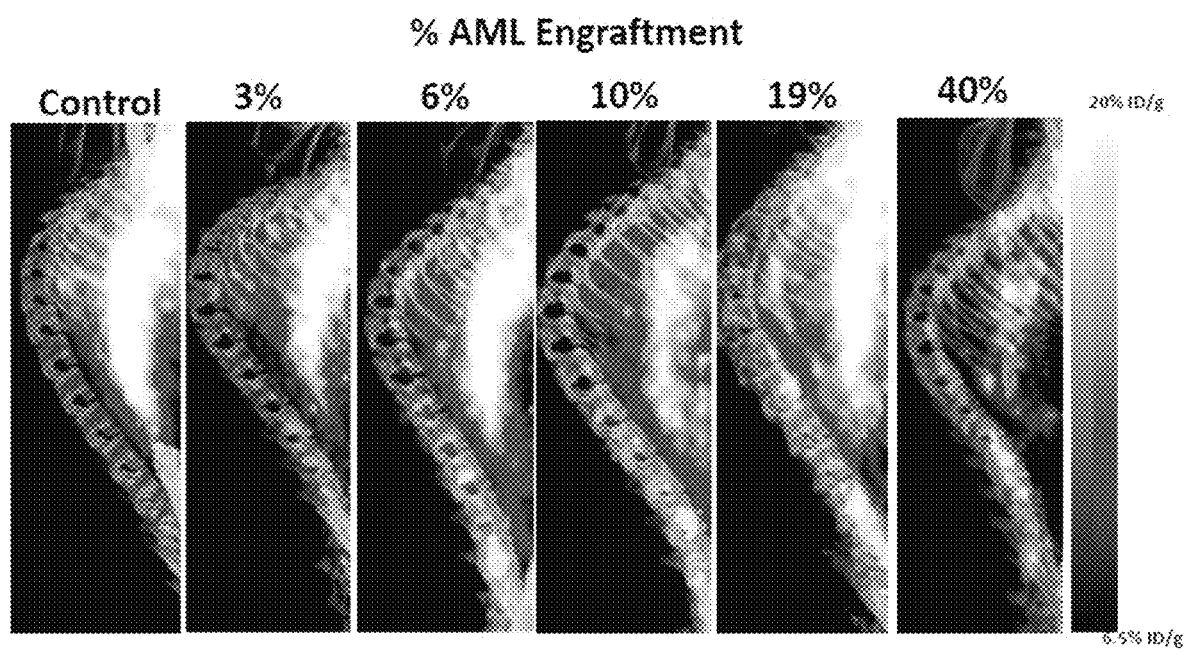

Besides detecting a CD33+ specific signal, anti-CD33 PET/CT imaging also indicated the spatial heterogeneity of AML. CD33+ PET activity was significantly heterogeneous within the femur; for example, the distal and proximal femur showed higher CD33 activity compared to the long bone area (FIG. 7A) in mice with low leukemia burden; however, heightened activity in the long bone was observed when leukemic burden increased (FIG. 7A). A similar localization pattern was seen in other bones including the tibia, humerus and L-spine (FIG. 3D). CD33 activity was mostly concentrated in the proximal/distal end of the bone. Further supporting the spatial distribution of AML, in the L-spine (FIG. 7B) at areas of low leukemic burden (5-10%), the disease was strongly localized to one of the segments (L1-L5) of the L-spine. However, with increasing leukemic burden (>15%) the leukemia was distributed across the L-spine and could be seen even on the T-spine, which was initially undetectable in the low leukemia group (FIG. 7B), suggesting a preferential niche for AML during the early stages of disease progression. Therefore, the treatment of these localized leukemia regions using fTMI was evaluated.

Example 6: PET-CT Image-Guided fTMI

Figures 8A, 8B, 8C:
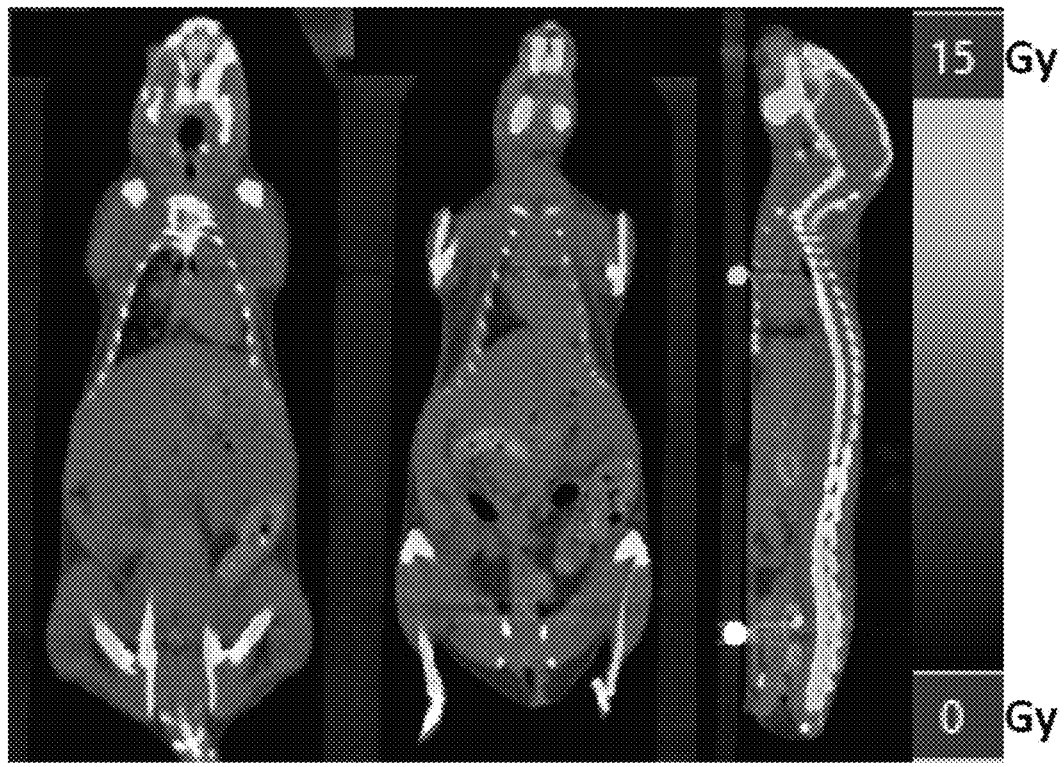
FIGS. 8A-8E show a functional total marrow irradiation (fTMI) treatment plan showing augmented dose painting. PET-CT images indicate CD33+ avid regions, and using these images a molecular image-guided fTMI treatment plan was developed. Two Gy TMI treatment with 2 Gy boost to: coronal slice of hip & shoulder joint regions (FIG. 8A), coronal slice of knee & elbow joint regions (FIG. 8B), and sagittal slice of L spine region (FIG. 8C). Boosted CD33+ avid regions are shown with yellow color.
Figure 8D:
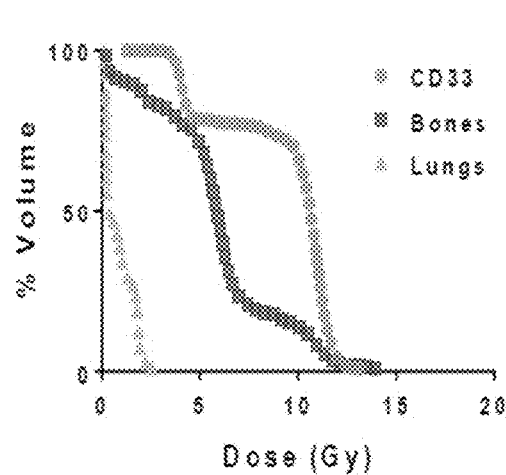
Figure 8E:
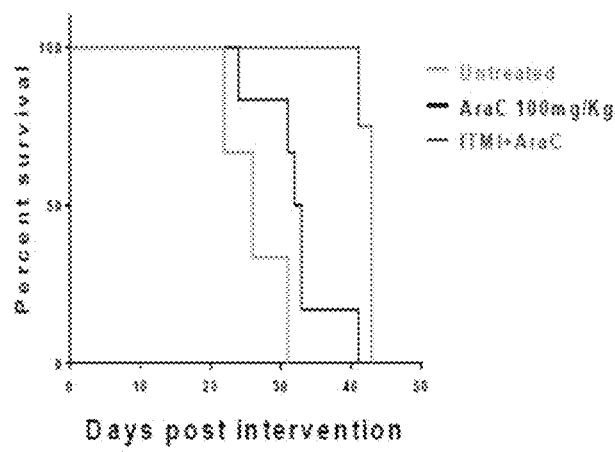

PET-CT images were used to design an fTMI treatment plan. The standard fTMI treatment plan of 2Gy TMI and a 2Gy boost to the CD33 enriched region is shown (FIGS. 8A-8C). The dose-volume histograms (DVH) for the fTMI plan (n=5) clearly show that bones received considerably high radiation doses while the vital organs (viz lung) received minimal doses in the fTMI plan (FIG. 8D). Table 1 and 2 show volumes and mean dose for the CD33-avid regions, the entire skeletal (bone and marrow) system, and lungs for 5 mice. The mean dose to CD33 avid regions was ~1.5 times more than the entire skeletal system while the unintended soft tissue (lung) received less dose, suggesting increased cell killing in the disease regions and reduced radiation toxicity to other organs by fTMI (n=5). FIG. 8E shows that fTMI and AraC combined treatment increased survival of the mice by about 17 days and about 10 days comparing to untreated and AraC treated mice.

TABLE 1

| Units: cc | Bone (PTV) | CD33 | Lungs |
|---|---|---|---|
| Vol | 1088.40 | 96.60 | 416.60 |
| Std. Dev. | 113.15 | 10.69 | 94.12 |

TABLE 2

| Units: Gy | Bone (PTV) | CD33 | Lungs |
|---|---|---|---|
| Dmean | 5.78 | 8.23 | 1.02 |
| Std. Dev. | 0.31 | 0.64 | 0.21 |

Figure 9A:
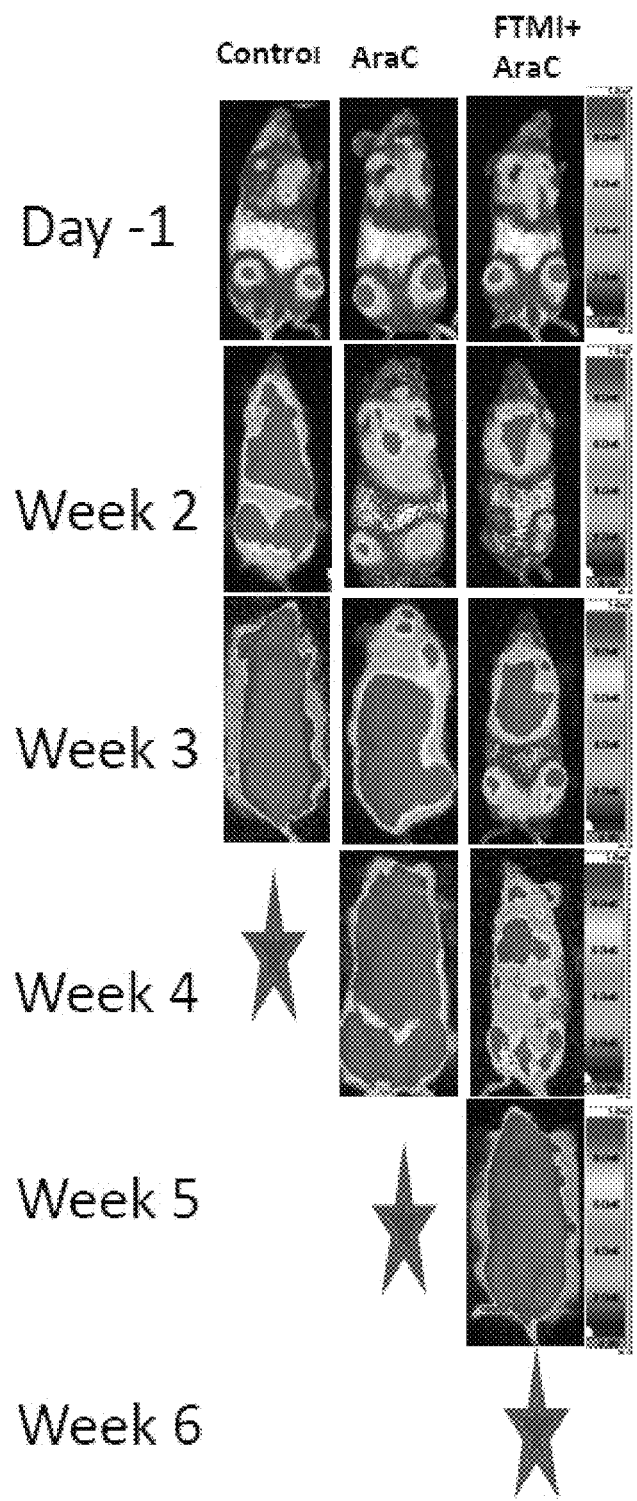
FIGS. 9A-9C show an fTMI treatment in immuno-compromised (NSG) and immuno-competent (B6) mouse models. fTMI in combination with chemotherapy was effective in reducing the disease burden and increasing survival of AML bearing mice in both model systems.
Figure 9B:
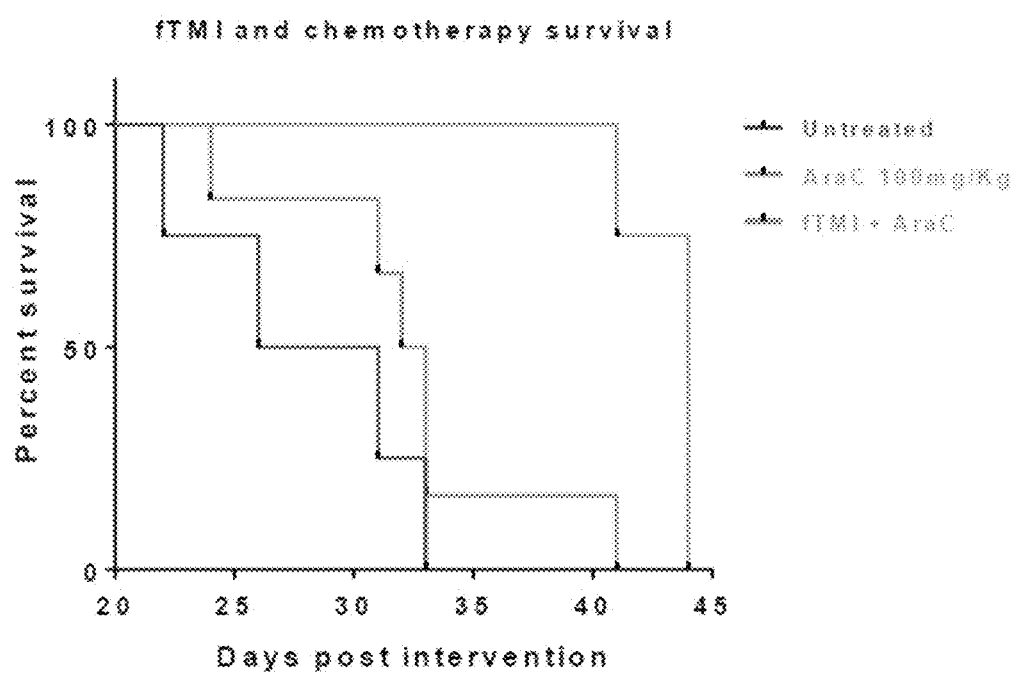
Figure 9C:
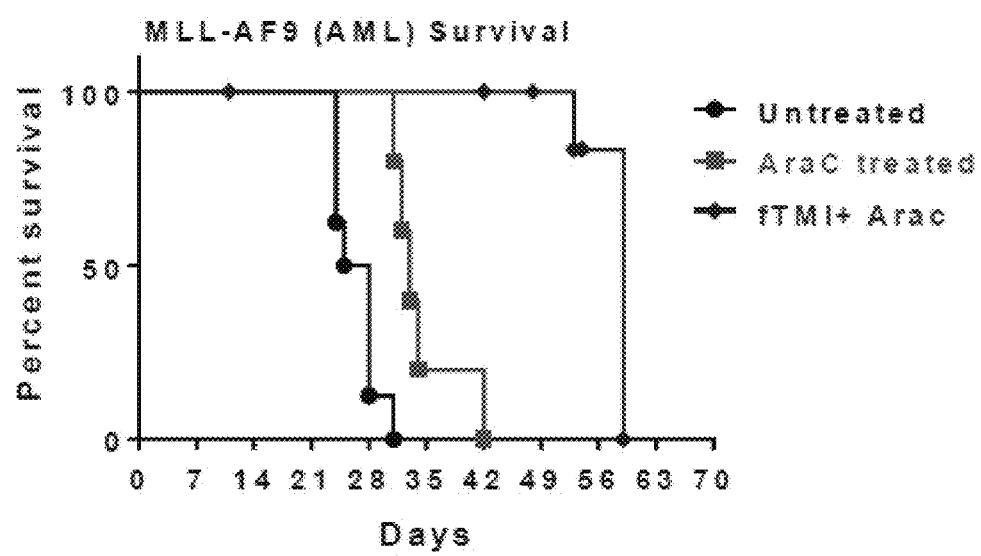

The leukemic burden (measured by BLI) 10 days post intervention was reduced in fTMI treated mice, correlating with an increase in survival compared with the control (FIG. 9A). fTMI in combination with chemotherapy increased the survival of AML-bearing mice by about 15 days and about 10 days longer than that in untreated or mice treated with AraC only, respectively (FIG. 9B). To circumvent the limitation of dose escalation present with the use of NSG mice, the B6 murine AML model was used. The fTMI treatment plan was 6 Gy TMI and a 3 Gy boost, each delivered in two fractions (total 12 Gy TMI and 6 Gy boost). The boost regions were extrapolated from the CD33 PET imaging. Mice given both fTMI and chemotherapy survived for about 59 days, whereas the conventional chemotherapy (AraC)-treated mice and untreated mice survived for only 33 and 26.5 days, respectively (FIG. 9C).

Example 7: Humanized CD33 Antibody Detects CD33 AML

Figure 10:
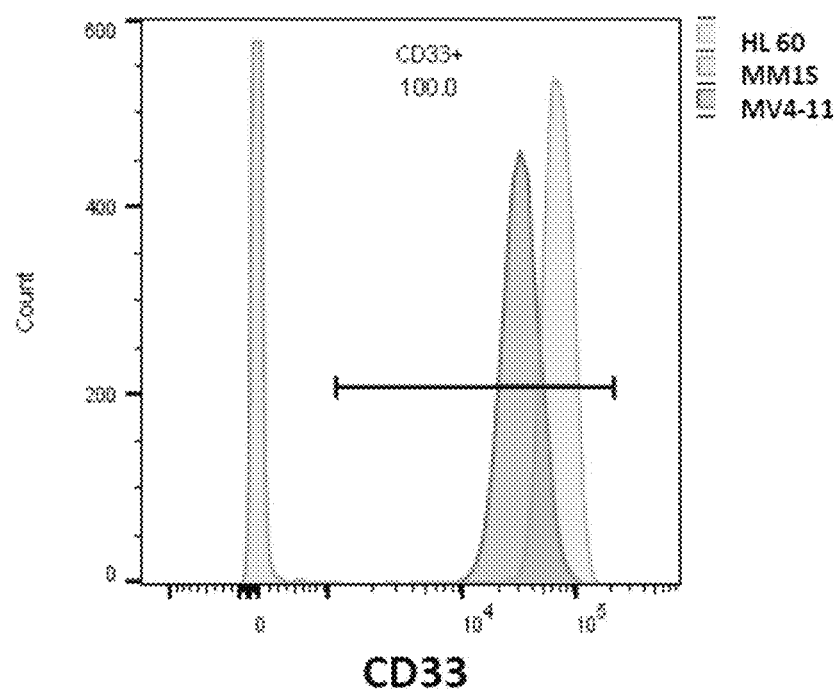
FIG. 10 shows humanized anti-CD33 immunoreactivity in AML cell line. The humanized anti-CD33 antibody detected CD33 in both AML cells but not in CD33-MM.1S.
Figure 10:
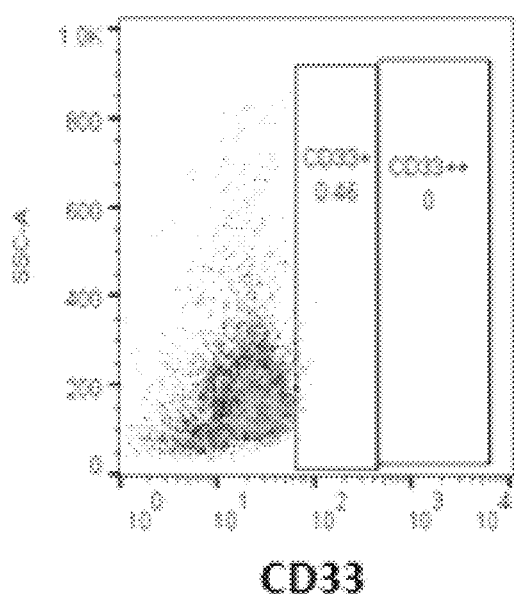
Figure 10:
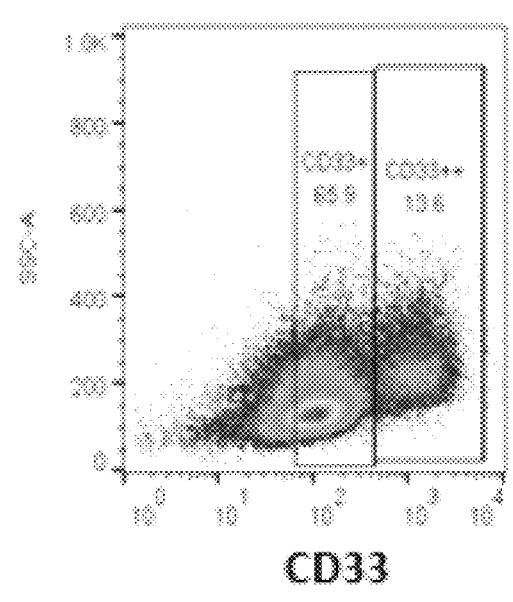

A humanized anti-CD33 mAb was developed, as described in Example 1. The humanized $^{64}$Cu-DOTA anti-human CD33 mAb immunoreactivity was tested and it was found that the humanized $^{64}$Cu-DOTA anti-human CD33 mAb bound specifically to CD33 positive AML cell lines (MV4-11, HL-60) (FIG. 10).

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Hassan C, Afshinnekoo E, Li S, Wu S, Mason C E. Genetic and epigenetic heterogeneity and the impact on cancer relapse. Exp Hematol. 2017; 54: 26-30.
2. Shah A, Andersson T M, Rachet B, Bjorkholm M, Lambert P C. Survival and cure of acute myeloid leukaemia in England, 1971-2006: a population-based study. Br J Haematol. 2013; 162: 509-16.
3. Mayer A T, Natarajan A, Gordon S R, Maute R L, McCracken M N, Ring A M, et al. Practical Immuno-PET Radiotracer Design Considerations for Human Immune Checkpoint Imaging. Journal of Nuclear Medicine. 2017; 58: 538-46.
4. Dohner H, Estey E H, Amadori S, Appelbaum F R, Buchner T, Burnett A K, et al. Diagnosis and management of acute myeloid leukemia in adults: recommendations from an international expert panel, on behalf of the European LeukemiaNet. Blood. 2010; 115: 453-74.
5. Ehninger A, Kramer M, Röllig C, Thiede C, Bornhäuser M, von Bonin M, et al. Distribution and levels of cell surface expression of CD33 and CD123 in acute myeloid leukemia. Blood Cancer Journal. 2014; 4: e218.

6. Pollard J A, Alonzo T A, Loken M, Gerbing R B, Ho P A, Bernstein I D, et al. Correlation of CD33 expression level with disease characteristics and response to gemtuzumab ozogamicin containing chemotherapy in childhood AML. Blood. 2012; 119: 3705-11.
7. Griffeth L K. Use of PET/CT scanning in cancer patients: technical and practical considerations. Proceedings (Baylor University Medical Center). 2005; 18: 321-30.
8. Kal H B, Loes van Kempen-Harteveld M, Heijenbrok-Kal M H, Struikmans H. Biologically effective dose in total-body irradiation and hematopoietic stem cell transplantation. Strahlenther Onkol. 2006; 182: 672-9.
9. Clift R A, Buckner C D, Appelbaum F R, Bearman S I, Petersen F B, Fisher L D, et al. Allogeneic marrow transplantation in patients with acute myeloid leukemia in first remission: a randomized trial of two irradiation regimens. Blood. 1990; 76: 1867-71.
10. Stein A, Palmer J, Tsai N C, Al Malki M M, Aldoss I, Ali H, et al. Phase I Trial of Total Marrow and Lymphoid Irradiation Transplantation Conditioning in Patients with Relapsed/Refractory Acute Leukemia. Biol Blood Marrow Transplant. 2017; 23: 618-24.
11. Magome T, Froelich J, Holtan S G, Takahashi Y, Verneris M R, Brown K, et al. Whole-Body Distribution of Leukemia and Functional Total Marrow Irradiation Based on FLT-PET and Dual-Energy CT. Molecular Imaging. 2017; 16: 1536012117732203.
12. Appelbaum F R, Matthews D C, Eary J F, Badger C C, Kellogg M, Press O W, et al. The use of radiolabeled anti-CD33 antibody to augment marrow irradiation prior to marrow transplantation for acute myelogenous leukemia. Transplantation. 1992; 54: 829-33.
13. van der Jagt R H, Badger C, Appelbaum F R, Press O W, Matthews D C, Eary J F, et al. Localization of radiolabeled antimyeloid antibodies in a human acute leukemia xenograft tumor model. Cancer Res. 1992; 52: 89-94.
14. Caron P C, Co M S, Bull M K, Avdalovic N M, Queen C, Scheinberg D A. Biological and immunological features of humanized M195 (anti-CD33) monoclonal antibodies. Cancer Res. 1992; 52: 6761-7.
15. Co M S, Avdalovic N M, Caron P C, Avdalovic M V, Scheinberg D A, Queen C. Chimeric and humanized antibodies with specificity for the CD33 antigen. J Immunol. 1992; 148: 1149-54.
16. Caserta E, Chea J, Minnix M, Viola D, Vonderfecht S, Yazaki P, et al. Copper 64-labeled daratumumab as a PET/CT imaging tracer for multiple myeloma. Blood. 2018; 131: 741-5.
17. van Hoof S J, Granton P V, Verhaegen F. Development and validation of a treatment planning system for small animal radiotherapy: SmART-Plan. Radiother Oncol. 2013; 109: 361-6.
18. Stölzel F, Röllig C, Radke J, Mohr B, Platzbecker U, Bornhäuser M, et al. (18)F-FDG-PET/CT for detection of extramedullary acute myeloid leukemia. Haematologica. 2011; 96: 1552-6.
19. Arimoto M K, Nakamoto Y, Nakatani K, Ishimori T, Yamashita K, Takaori-Kondo A, et al. Increased bone marrow uptake of 18F-FDG in leukemia patients: preliminary findings. Springerplus. 2015; 4: 521.
20. Han E J, Lee B H, Kim J A, Park Y H, Choi W H. Early assessment of response to induction therapy in acute myeloid leukemia using (18)F-FLT PET/CT. EJNMMI Res. 2017; 7: 75.
21. Cribe A S, Steenhof M, Marcher C W, Petersen H, Frederiksen H, Friis L S. Extramedullary disease in patients with acute myeloid leukemia assessed by 18F-FDG PET. Eur J Haematol. 2013; 90: 273-8.
22. Riad R, Omar W, Sidhom I, Zamzam M, Zaky I, Hafez M, et al. False-positive F-18 FDG uptake in PET/CT studies in pediatric patients with abdominal Burkitt's lymphoma. Nucl Med Commun. 2010; 31: 232-8.
23. Long N M, Smith C S. Causes and imaging features of false positives and false negatives on F-PET/CT in oncologic imaging. Insights Imaging. 2011; 2: 679-98.
24. Williams K M, Holter-Chakrabarty J L, Lindenberg L, Adler S, Chai A, Kurdziel K, et al. Novel PET Imaging with Fluorothymidine (FLT) Predicts Relapse Quantitatively at Day 28 Post Transplantation in Patients with Acute Leukemia. Biology of Blood and Marrow Transplantation. 2016; 22: S213-S4.
25. Godwin C D, McDonald G B, Walter R B. Sinusoidal obstruction syndrome following CD33-targeted therapy in acute myeloid leukemia. Blood. 2017; 129: 2330-2.
26. Mallampati S, Sun B, Lu Y, Ma H, Gong Y, Wang D, Lee J S, Lin K, Sun X. Integrated genetic approaches identify the molecular mechanisms of Sox4 in early B-cell development: intricate roles for RAG1/2 and CK1epsilon. Blood. 2014; 123: 4064-4076.

What is claimed is:

1. A non-invasive method of in vivo detecting acute myeloid leukemia (AML) or extramedullary disease (EMD) in a subject, comprising:
    administering to the subject an effective dose of a radioactive isotope-labeled anti-CD33 antibody;
    exposing the subject to positron emission tomography-computed tomography (PET-CT) scanning; and
    detecting CD33− PET-CT signal in tissue or organ of the subject, thereby to determine the presence of the AML cancer cells or the EMD cancer cells, wherein the anti-CD33 antibody comprises a light chain comprising an amino acid sequence encoded by nucleotides 69-725 of SEQ ID NO: 1 and a heavy chain comprising an amino acid sequence encoded by nucleotides 67-1407 of SEQ ID NO: 2.

2. The method of claim 1, wherein the PET-CT scanning is carried out about 6 hours, about 12 hours, about 18 hours, about 24 hours, about 30 hours, about 36 hours, or about 48 hours after administration of the radioactive isotope-labeled anti-CD33 antibody.

3. The method of claim 1, wherein the radioactive isotope-labeled anti-CD33 antibody is administered to the subject by intravenous injection, subcutaneous injection, or peritoneal injection.

4. The method of claim 1, wherein the radioactive isotope is conjugated to the anti-CD33 antibody via a chelating agent.

5. The method of claim 4, wherein the chelating agent is 1,4,7,10-tetraazacyclododecane-1,4,7,10-tetraacetic acid (DOTA).

6. The method of claim 1, wherein the radioactive isotope is $^{64}$Cu.

7. A method of determining heterogenicity in the spatial distribution of acute myeloid leukemia (AML) in a subject, comprising:
    administering to the subject an effective dose of a radioactive isotope-labeled anti-CD33 antibody;
    exposing the subject to PET-CT scanning; and
    detecting CD33− PET-CT signal in tissue or organ of the subject, thereby to determine the heterogenicity in the spatial distribution of AML, wherein the anti-CD33 antibody comprises a light chain comprising an amino acid sequence encoded by nucleotides 69-725 of SEQ ID NO: 1 and a heavy chain comprising an amino acid sequence encoded by nucleotides 67-1407 of SEQ ID NO: 2.

8. The method of claim 7, wherein the PET-CT scanning is carried out about 6 hours, about 12 hours, about 18 hours, about 24 hours, about 30 hours, about 36 hours, or about 48 hours after administration of the radioactive isotope-labeled anti-CD33 antibody.

9. The method of claim 7, wherein the radioactive isotope-labeled anti-CD33 antibody is administered to the subject by intravenous injection, subcutaneous injection, or peritoneal injection.

10. The method of claim 7, wherein the radioactive isotope is conjugated to the anti-CD33 antibody via 1,4,7,10-tetraazacyclododecane-1,4,7,10-tetraacetic acid (DOTA), or wherein the radioactive isotope is $^{64}$Cu.

11. A method of treating acute myeloid leukemia (AML) or extramedullary disease (EMD) in a subject, comprising:
    administering to a subject an effective dose of a radioactive isotope-labeled anti-CD33 antibody;
    exposing the subject to positron emission tomography-computed tomography (PET-CT) scanning;
    detecting CD33+ PET-CT signal in tissue or organ of the subject to determine the presence of the cancer cells; and
    administering functional total marrow irradiation (fTMI) therapy to the subject based on the distribution of the CD33+ PET-CT signal,
    wherein the tissue or organ with a higher intensity of the CD33+ PET-CT signal receives a higher dose, a higher frequency, or a longer exposure of the fTMI therapy than the tissue or organ with a lower intensity of the CD33+ PET-CT signal, wherein the anti-CD33 antibody comprises a light chain comprising an amino acid sequence encoded by nucleotides 69-725 of SEQ ID NO: 1 and a heavy chain comprising an amino acid sequence encoded by nucleotides 67-1407 of SEQ ID NO: 2.

12. The method of claim 11, the vital organs, or the tissue or organ having no CD33+ PET-CT signal does not receive any fTMI therapy.

13. The method of claim 11, further comprising administering to the subject a chemotherapy before or after the fTMI therapy.

14. The method of claim 13, wherein the combination of the fTMI therapy and the chemotherapy results in a reduced dose, frequency, and/or intensity of the fTMI therapy or the chemotherapy comparing to each of the therapies used alone.

15. The method of claim 13, wherein the chemotherapy is AraC.

16. The method of claim 11, the PET-CT scanning is carried out about 6 hours, about 12 hours, about 18 hours, about 24 hours, about 30 hours, about 36 hours, or about 48 hours after administration of the radioactive isotope-labeled anti-CD33 antibody.

17. The method of claim 11, further comprising transplanting bone marrow to the subject.

18. The method of claim 11, wherein the radioactive isotope-labeled anti-CD33 antibody is administered to the subject by intravenous injection, subcutaneous injection, or peritoneal injection.

19. The method of claim 11, wherein the radioactive isotope is conjugated to the anti-CD33 antibody via a chelating agent, or wherein the radioactive isotope is $^{64}$Cu.

20. The method of claim 19, wherein the chelating agent is 1,4,7,10-tetraazacyclododecane-1,4,7,10-tetraacetic acid (DOTA).

\* \* \* \* \*

SEQUENCE LISTING

```
<160> NUMBER OF SEQ ID NOS: 2

<210> SEQ ID NO 1
<211> LENGTH: 725
<212> TYPE: DNA
<213> ORGANISM: Artificial Sequence
<220> FEATURE:
<223> OTHER INFORMATION: huM195 (alpha-CD33) light chain
<220> FEATURE:
<221> NAME/KEY: misc_feature
<222> LOCATION: (1)..(8)
<223> OTHER INFORMATION: Kozak sequence
<220> FEATURE:
<221> NAME/KEY: misc_feature
<222> LOCATION: (9)..(68)
<223> OTHER INFORMATION: leader signal sequence
```

-continued

```
<400> SEQUENCE: 1
ccgccaccat ggaaaccgac acactgctgc tgtgggtgct gcttttgtgg gtgccaggct      60
ctaccggcga catccagatg acacagagcc cttctagcct gagcgcctct gtgggcgata    120
gagtgaccat cacatgtaga gccagcgaga gcgtggacaa ctacggcatc agcttcatga    180
actggttcca gcagaagccc ggcaaggccc taaactgct gatctacgcc gccagcaatc     240
aaggcagcgg agtgcctagc agattttctg cagcggctc tggcaccgac ttcaccctga    300
caattagcag cctgcagcct gacgacttcg ccacctacta ctgccagcag tctaaagagg    360
tgccctggac ctttggacag ggcaccaagg tggaaatcaa gagaacagtg gccgctccga    420
gcgtgttcat cttt ccacca gcgacgagc agctgaaaag cggagccgct tctgtcgtgt    480
gcctgctgaa caacttctac cccagagaag ccaaggtgca gtggaaggtg gacaatgccc    540
tgcagagcgg caatagccaa gagagcgtga ccgagcagga cagcaaggat agcacataca    600
gcctgagcag cacactgacc ctgagcaagg ccgactacga gaagcacaaa gtgtacgcct    660
gcgaagtgac acaccaggc ctgtctagcc ctgtgaccaa gagcttcaac cggggcgagt    720
gttga                                                                725

<210> SEQ ID NO 2
<211> LENGTH: 1407
<212> TYPE: DNA
<213> ORGANISM: Artificial Sequence
<220> FEATURE:
<223> OTHER INFORMATION: huM195 (alpha-CD33) heavy chain
<220> FEATURE:
<221> NAME/KEY: misc_feature
<222> LOCATION: (1)..(9)
<223> OTHER INFORMATION: Kozak sequence
<220> FEATURE:
<221> NAME/KEY: misc_feature
<222> LOCATION: (10)..(66)
<223> OTHER INFORMATION: signal sequence

<400> SEQUENCE: 2
gccgccacca tgaagtgcag ctgggtcatc ttctttctga tggccgtggt caccggcgtg     60
aactctcagg ttcaactggt gcagtctggc gccgaagtga agaaacctgg cagctctgtg    120
aaggtgtcct gcaaggccag cggctacacc tttaccgact acaacatgca ctgggtccga    180
caggctccag acagggact cgagtggatc ggctacatct acccttacaa tggcggcacc    240
ggctacaacc agaagttcaa gagcaaggcc accatcaccg ccgacgagag cacaaacaca    300
gcctacatga aactgagcag cctgagaagc gaggacaccg ccgtgtacta ttgtgccaga    360
ggcagacccg ccatggatta ttggggacag ggcaccctgg ttaccgtgtc tagcgcctct    420
acaaagggcc ctagtgtgtt ccctctggct cctagcagca gagcacatc tggtggaaca    480 gccgctctgg gctgcctggt caaggattac tttcctgagc ctgtgaccgt gtcctggaat    540
agcggagcac tgacaagcgg cgtgcacaca tttccagctg tgctgcagag cagcggcctg    600
tactctctgt ctagcgtggt cacagtgcct agctctagcc tgggcaccca gacctacatc    660
tgcaacgtga accacaagcc tagcaacacc aaggtggaca gaaggtgga acccaagagc    720 tgcgacaaga cccacacctg tcctccatgt cctgctccag aactgctcgg cggaccctcc    780
gttttcctgt ttccacctaa gcctaaggac accctgatga tcagcagaac ccctgaagtg    840
acctgcgtgg tggtggatgt gtcccacgag gaccagaaga tgaagttcaa ttggtacgtg    900
gacggcgtgg aagtgcacaa cgccaagacc aagcctagag aggaacagta caacagcacc    960
```

| | | | | | |
|---|---|---|---|---|---|
| tacagagtgg | tgtccgtgct | gaccgtgctg | caccaggatt | ggctgaacgg | caaagagtac | 1020
| aagtgcaagg | tgtccaacaa | ggctctgccc | gctcctatcg | agaaaaccat | ctccaaggcc | 1080
| aagggccagc | caagagaacc | ccaggtttac | acactgcctc | caagcaggga | cgagctgacc | 1140
| aagaatcagg | tgtccctgac | ctgcctcgtg | aagggcttct | acccttccga | tatcgccgtg | 1200
| gaatgggaga | gcaatggaca | gcccgagaac | aactacaaga | caacccctcc | tgtgctggac | 1260
| agcgacggct | cattcttcct | gtacagcaag | ctgacagtgg | acaagtccag | atggcagcag | 1320
| ggcaacgtgt | tcagctgttc | tgtgatgcac | gaggccctgc | acaaccacta | cacccagaaa | 1380
| agcctgtctc | tgagccccgg | caaatga | | | | 1407